(12) United States Patent
Daly

(10) Patent No.: US 8,074,646 B2
(45) Date of Patent: Dec. 13, 2011

(54) METHOD AND SYSTEM FOR CONTROLLING BREATHING

(76) Inventor: Robert W. Daly, Weston, MA (US)

(*) Notice: Subject to any disclaimer, the term of this patent is extended or adjusted under 35 U.S.C. 154(b) by 1126 days.

(21) Appl. No.: 11/787,854

(22) Filed: Apr. 17, 2007

(65) Prior Publication Data

US 2007/0255160 A1 Nov. 1, 2007

Related U.S. Application Data

(63) Continuation-in-part of application No. 11/405,948, filed on Apr. 17, 2006.

(51) Int. Cl.
*A62B 7/00* (2006.01)
*A61M 16/00* (2006.01)

(52) U.S. Cl. ............... 128/204.18; 128/911; 128/914; 128/205.28

(58) Field of Classification Search .......... 128/201.28, 128/204.18, 204.21, 204.22, 205.12, 205.24, 128/205.28, 204.23, 205.19; 600/529, 538
See application file for complete search history.

(56) References Cited

U.S. PATENT DOCUMENTS

| | | | |
|---|---|---|---|
| 2,809,633 A | 10/1957 | Sweringen et al. | |
| 2,291,581 A | 1/1960 | Sweringen et al. | |
| 3,357,426 A | 12/1967 | Cohen et al. | |
| 4,112,938 A | 9/1978 | Jeretin | 128/204.23 |
| 4,188,946 A | 2/1980 | Watson et al. | 128/204.22 |
| 4,265,235 A | 5/1981 | Fukunaga | 128/200.24 |
| 4,467,799 A | 8/1984 | Steinberg | 128/106.14 |
| 4,648,398 A | 3/1987 | Agdanowski et al. | 128/207.18 |
| 5,320,093 A | 6/1994 | Raemer | 128/203.12 |
| 5,540,219 A | 7/1996 | Mechlenburg et al. | 128/204.23 |
| 5,540,223 A | 7/1996 | Starr et al. | 128/205.25 |
| 5,647,345 A | 7/1997 | Saul | 128/201.23 |
| 5,676,133 A | 10/1997 | Hickle et al. | 128/205.12 |
| 5,755,225 A | 5/1998 | Hutson | 128/207.18 |

(Continued)

FOREIGN PATENT DOCUMENTS

EP 0861672 9/1998

(Continued)

OTHER PUBLICATIONS

Lorenzi-Filho, et al. (1999), "Effects of Inhaled Carbon Dioxide and Oxygen on Cheyne-Stokes Respiration in Patients with Heart Failure", *American Journal of Respiratory and Critical Care Medicine*, 159:1490-1498.

(Continued)

*Primary Examiner* — Justine Yu
*Assistant Examiner* — Valerie L Skorupa
(74) *Attorney, Agent, or Firm* — Mintz Levin Ferris Glovsky and Popeo, P.C.; Ingrid A. Beatti

(57) ABSTRACT

The present invention relates to a method and a system for controlling breathing of a patient. A system for controlling breathing of a patient includes a respiratory conduit. The respiratory conduit is configured to be coupled to a patient interface device and is further configured to be coupled to a pressurized air generating device. The respiratory conduit includes at least two air flow control devices, positioned between the patient interface device and the pressurized air generating device. The respiratory conduit includes at least two volumes, wherein one volume is positioned between a first air flow control device and a second air flow control device and another volume is positioned between a second air flow control device and a third air flow control device.

33 Claims, 23 Drawing Sheets

U.S. PATENT DOCUMENTS

| | | | | |
|---|---|---|---|---|
| 5,794,615 | A | 8/1998 | Estes | 128/204.23 |
| 5,901,704 | A | 5/1999 | Estes et al. | 128/204.23 |
| 5,918,598 | A | 7/1999 | Belfer et al. | 128/206.25 |
| 6,003,511 | A | 12/1999 | Fukunaga et al. | 128/202.27 |
| 6,009,871 | A | 1/2000 | Kiske et al. | 128/204.21 |
| 6,196,223 | B1 | 3/2001 | Belfer et al. | 128/206.25 |
| 6,227,196 | B1 | 5/2001 | Jaffe et al. | 128/200.26 |
| 6,298,848 | B1 | 10/2001 | Skog | 128/204.18 |
| 6,306,098 | B1 | 10/2001 | Orr et al. | 128/200.26 |
| 6,318,362 | B1 | 11/2001 | Johnson | 128/200.24 |
| 6,341,606 | B1 | 1/2002 | Bordewick et al. | 128/206.25 |
| 6,349,721 | B1* | 2/2002 | Grilliot et al. | 128/201.29 |
| 6,354,292 | B1 | 3/2002 | Fisher | 128/203.12 |
| 6,363,933 | B1 | 4/2002 | Berthon-Jones | 128/204.23 |
| 6,367,474 | B1 | 4/2002 | Berthon-Jones et al. | 128/204.23 |
| 6,397,847 | B1 | 6/2002 | Scarberry et al. | 128/206.24 |
| 6,439,231 | B1 | 8/2002 | Fukunaga et al. | 128/207.14 |
| 6,467,477 | B1 | 10/2002 | Frank et al. | 128/203.23 |
| 6,494,206 | B1 | 12/2002 | Bergamaschi et al. | 128/206.24 |
| 6,584,977 | B1 | 7/2003 | Serowski | 128/206.24 |
| 6,591,835 | B1* | 7/2003 | Blanch | 128/204.25 |
| 6,599,252 | B2 | 7/2003 | Starr | 600/532 |
| 6,609,517 | B1 | 8/2003 | Estes et al. | 128/204.23 |
| 6,612,308 | B2 | 9/2003 | Fisher et al. | 128/205.11 |
| 6,615,831 | B1* | 9/2003 | Tuitt et al. | 128/204.18 |
| 6,622,725 | B1 | 9/2003 | Fisher et al. | 128/200.24 |
| 6,629,527 | B1 | 10/2003 | Estes et al. | 128/204.18 |
| 6,640,806 | B2 | 11/2003 | Yurko | 128/204.23 |
| 6,752,150 | B1 | 6/2004 | Remmers et al. | 128/204.18 |
| 6,752,151 | B2 | 6/2004 | Hill | 128/204.18 |
| 6,799,570 | B2 | 10/2004 | Fisher et al. | 128/200.24 |
| 6,851,429 | B2 | 2/2005 | Bishop | 128/206.25 |
| 6,908,438 | B2* | 6/2005 | Orr et al. | 600/532 |
| 6,948,499 | B2 | 9/2005 | Griesbach et al. | 128/206.25 |
| 6,951,217 | B2 | 10/2005 | Berthon-Jones | 128/206.25 |
| 7,017,577 | B2 | 3/2006 | Matich | 128/206.14 |
| 7,073,501 | B2* | 7/2006 | Remmers et al. | 128/204.18 |
| 7,077,138 | B2 | 7/2006 | Bateman et al. | 128/206.14 |
| 2001/0035182 | A1 | 11/2001 | Rubin et al. | 128/200.23 |
| 2001/0054422 | A1* | 12/2001 | Smith et al. | 128/200.24 |
| 2002/0059933 | A1 | 5/2002 | Jaffe et al. | 128/204.22 |
| 2002/0185129 | A1* | 12/2002 | Fisher et al. | 128/203.25 |
| 2003/0145855 | A1* | 8/2003 | Fuhrman et al. | 128/204.18 |
| 2003/0217746 | A1 | 11/2003 | Lewis et al. | 128/201.26 |
| 2004/0016433 | A1 | 1/2004 | Estes et al. | 128/204.21 |
| 2004/0035422 | A1 | 2/2004 | Truitt et al. | 128/204.18 |
| 2004/0144383 | A1 | 7/2004 | Thomas et al. | 128/204.18 |
| 2004/0206354 | A1 | 10/2004 | Fisher et al. | 128/204.23 |
| 2005/0015036 | A1 | 1/2005 | Lutri et al. | 602/41 |
| 2005/0066976 | A1 | 3/2005 | Wondka | 128/207.18 |
| 2006/0096598 | A1* | 5/2006 | Ho et al. | 128/206.24 |

FOREIGN PATENT DOCUMENTS

| | | |
|---|---|---|
| FR | 1555589 | 1/1969 |
| FR | 2827778 | 1/2003 |
| WO | WO 97/10869 | 3/1997 |
| WO | 9952581 A1 | 10/1999 |
| WO | WO 00/45882 | 10/2000 |
| WO | WO 2007/130067 | 11/2007 |

OTHER PUBLICATIONS

Vesely, et al., "A simple, effective method for controlling end tidal $PCO_2$, for MRI mapping of cerebrovascular reactivity", *The Isocapnia Research Laboratory*, http://www.isocapnia.com/Fine%20Control%20of%20PCO2%20and%20PO2.htm.

Vesely, et al. (2003), "*Isocapnic hyperpnoea* accelerates recovery from isoflurane anaesthesia", *British Journal of Anaesthesia*, 91 6:787-92.

International Search Report dated Sep. 2, 2004 for PCT/US03/37236.

"Nasal airflow dynamics: mechanisms and response associated with an external nasal dilator strip," J.P. Kirkness, J.R. Wheatley and T.C. Amis, European Respiratory Journal 2000; 15:929-936.

"Effect of jaw position and posture on forced inspiratory airflow in normal subjects and patients with obstructive sleep apnea," by S. Masumi et al., Chest 1996; 109:1484-1489.

International Search Report and Written Opinion for PCT/US08/06612 dated Oct. 1, 2008.

International Search Report for PCT/US2007/009454 dated Oct. 30, 2008.

Notification of Transmittal of The International Search Report and The Written Opinion of the International Searching Authority, or the Declaration dated Jul. 23, 2009.

* cited by examiner

METHOD AND SYSTEM FOR CONTROLLING BREATHING

CROSS-REFERENCE TO RELATED APPLICATIONS

This application is a continuation-in-part of U.S. patent application Ser. No. 11/405,948, filed Apr. 17, 2006, which is herein incorporated by reference in its entirety.

BACKGROUND OF THE INVENTION

1. Field of the Invention

The present invention relates generally to treatment of breathing disorders. In particular, the present invention relates to systems and methods for controlling breathing of a patient by maintaining specific levels of carbon dioxide ("$CO_2$") dissolved in the patient's arterial blood.

BACKGROUND OF THE INVENTION

Sleep-disordered breathing ("SDB") includes all syndromes that pose breathing difficulties during sleep. These include obstructive sleep apnea ("OSA"), mixed sleep apnea ("MSA"), central sleep apnea ("CSA"), Cheyne-Stokes respiration ("CSR"), and others. Some form of SDB occurs in approximately 3-5% of the U.S. population.

While anatomical problems such as obesity or an abnormally narrow upper airway may be a cause of some SDB, neurological difficulties in controlling levels of blood gases, such as $CO_2$ and oxygen ("$O_2$"), are increasingly being recognized as important contributors to the disease. This is especially true of the "central" syndromes, MSA, CSA and CSR, which may account for as much as 20% of all SDB. Changes in the neurological system that controls the blood gases often produce unsteady respiratory patterns that cause arousals from sleep. These changes are accompanied by severe spikes in blood pressure and release of stress hormones that can cause long-term damage to a number of organ systems. Additionally, some SDB syndromes involve abnormal overall levels of blood gases. For example, low levels of dissolved $CO_2$ in arterial blood are frequently encountered, which represents a clinical problem. Thus, there is a need to stabilize respiration and establish appropriate blood gas levels by restoring normal control of blood gases when treating SDB.

SUMMARY OF THE INVENTION

The present invention relates to a system for controlling breathing of a patient. The system includes a respiratory conduit. The respiratory conduit is configured to be coupled to a patient interface device. The respiratory conduit is further configured to be coupled to a pressurized air generating device. The respiratory conduit includes at least two air flow control devices, positioned between the patient interface device and the pressurized air generating device. The respiratory conduit includes at least two volumes, wherein one volume is positioned between a first air flow control device and a second air flow control device and another volume is positioned between a second air flow control device and a third air flow control device. The second airflow control device configured to control evacuation of air from an airflow control conduit that is further configured to include multiple openings.

In some embodiments, the present invention relates to a method for controlling flow of carbon dioxide to a patient. The method includes controlling a level of carbon dioxide in blood of the patient using the system discussed above. The controlling includes measuring airflow through at least one of the airflow control devices, detecting a content of carbon dioxide in the measured airflow, adjusting airflow through at least one other one of the airflow control devices based on the detecting of the concentration of carbon dioxide, and adjusting sizes of the volumes based on the detection of the concentration of carbon dioxide and the adjusting of the airflow through at least one of the air flow control devices.

In some embodiments, the present invention includes a respiratory conduit configured to be coupled to a patient interface device of the patient. The respiratory conduit is configured to be coupled to a pressurized air supply device, wherein the pressurized air supply device supplies air to the patient at the other end. The respiratory conduit includes a first valve located adjacent the patient interface device and includes a first opening configured to control escape of the gas during the breathing process, a second valve configured to withdraw air from at least one location within the respiratory conduit during the breathing process, a first volume connector connecting the first valve and the second valve and configured to control supply of gas to the patient during the breathing process, a third valve that includes a third opening configured to control escape of gas during the breathing process, a second volume connector connecting the second valve and the third valve and configured to allow withdrawal of air from at least one location within the second volume, and a third connector connecting the second valve and the air supply device.

In some alternate embodiments, the present invention relates to a method of controlling breathing of a patient, wherein air is supplied to the patient using a patient interface device coupled to an air supply device using a respiratory conduit that includes at least one valve configured to withdraw air from at least one openings disposed within at least one volume connector, wherein the valves and the volume connectors are positioned along the length of the respiratory conduit. The method includes determining a rate of production of gas generated by the patient, measuring a rate of flow and a concentration of gas at each of the controllable openings, adjusting the flow rate through the multiple openings based on the measuring, and adjusting sizes of the multiple volume connectors based on at least one of the determining and the measuring. The air supplied to the patient includes a mixture of air supplied by the air supply device and a gas generated by the patient.

In yet other alternate embodiments, the present invention relates to a method of controlling breathing of a patient, wherein air is supplied to the patient using a patient interface device coupled to an air supply device using a respiratory conduit that includes at least two air flow control devices, positioned between the patient interface device and a pressurized air generating device, and at least two volumes, wherein at least one volume is configured to allow withdrawal of air from at least one location within the volume using at least one of the air flow control devices. The method includes determining an average concentration of gas in the air flowing out of the second air flow control device, comparing the average concentration of gas to a predetermined setpoint value of concentration of gas, computing the difference between the average concentration and the predetermined setpoint value of concentration, and controlling the breathing of the patient by adjusting flow of air through the first air flow control device until the computed difference is substantially eliminated.

In yet other alternate embodiments, the present invention relates to a system for controlling breathing of a patient. The system includes a respiratory conduit. The respiratory conduit is configured to be coupled to a patient interface device. The respiratory conduit is further configured to be coupled to a pressurized air generating device. The respiratory conduit includes at least two volumes, positioned between the patient interface device and the pressurized air generating device. The respiratory conduit includes at least two air flow control devices, wherein the at least one airflow control device is configured to withdraw air from at least one location within the respiratory conduit.

Further features and advantages of the invention, as well as structure and operation of various embodiments of the invention, are disclosed in detail below will reference to the accompanying drawings.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION

Of the two blood gases, carbon dioxide ("$CO_2$") and oxygen ("$O_2$"), problems with neurological control of breathing during sleep are related to control of $CO_2$ than $O_2$. $CO_2$ is dissolved in blood, and together with bicarbonate ions determines blood pH. Excessive $CO_2$ causes the blood to become acidic, while a deficit in $CO_2$ will cause the blood to be alkaline. Since proteins need a stable pH environment in which to function, the $CO_2$ levels should be controlled within a narrow range that will yield a blood pH of about 7.4. This is accomplished by close matching of $CO_2$ excretion via the lungs to the endogenous $CO_2$ production that is the product of cellular metabolism.

Figure 7:
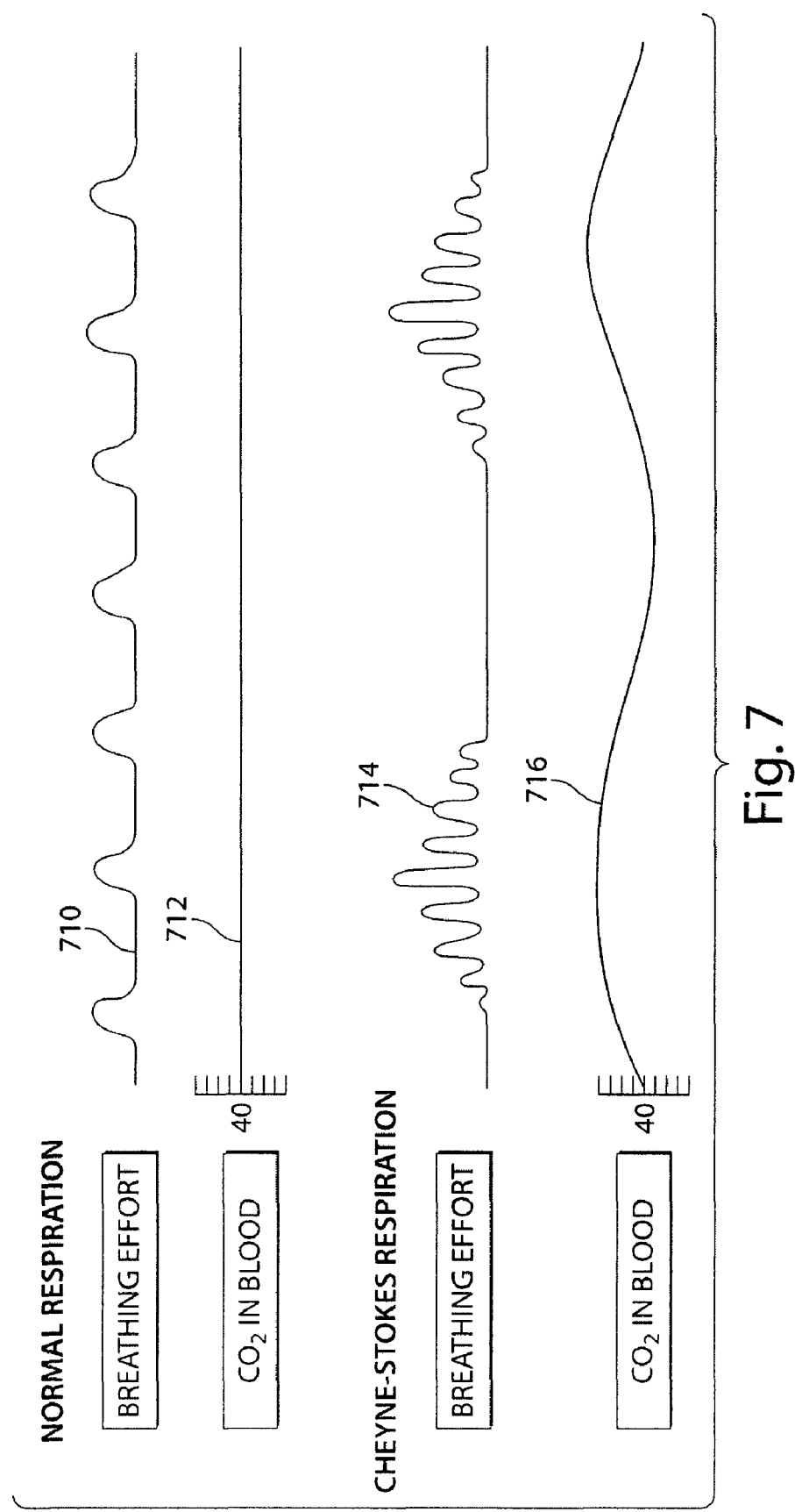
FIG. 7 is a graphical representation of a comparison between normal respiration and Cheyne-Stokes respiration.

FIG. 7 illustrates normal respiration and Cheyne-Stokes respiration plots along with corresponding $CO_2$ blood levels plots. During normal respiration, the breathing effort of a patient is steady, as shown by the plot 710. This corresponds to steady arterial $CO_2$ blood levels, shown in plot 712. A typical normal partial pressure of dissolved $CO_2$ in arterial blood is 40 mm Hg and $O_2$ pressure is approximately 105 mm Hg. During Cheyne-Stokes respiration, the breathing effort is erratic, as illustrated by the waxing/waning plot 714. A corresponding plot 716 shows the associated variable blood $CO_2$ levels during Cheyne-Stokes respiration.

A sensitive and finely tuned system detects blood $CO_2$ levels via a number of sensors, or chemoreceptors located within the vasculature and the brain of the patient. Nerve signaling from these sensors is processed by respiratory control centers in the brain, which send appropriate breathing pattern commands to the respiratory muscles including those of the diaphragm, chest and breathing airway. The goal of the system is to match the excretion of $CO_2$ with the production of $CO_2$ by varying the rate of respiration (both the depth and frequency of breathing). In healthy individuals, this system is accurate and steady. It is able to respond quickly to changes in $CO_2$ production and maintain blood $CO_2$ levels within a narrow range. Like many homeostatic mechanisms in the body, control of blood gases is accomplished by a closed-loop negative feedback control system.

When the system for controlling blood $CO_2$ becomes disordered, it can lose its ability to maintain steady $CO_2$ levels. It "chases" blood $CO_2$ in an oscillating pattern of "overshoot" and "undershoot", resulting in a characteristic waxing/waning respiratory pattern. CSR is the classic syndrome associated with this disordered respiratory patterning and it is common in the setting of a heart failure. FIG. 7 illustrates that normal breathing is accompanied by stable $CO_2$ levels in arterial blood while CSR exhibits oscillating breathing patterns due to unstable $CO_2$ levels.

Since the waxing/waning respiratory drive associated with poor control of blood gases applies also to control of the muscles holding the airway open, cyclic airway collapse during the waning epoch of respiratory drive is often a feature of these syndromes. In fact, pure waxing/waning respiratory patterns not associated with at least intermittent airway collapse are relatively rare and MSA may be the dominant expression of respiratory instability. MSA may present as an extremely regular and predictable pattern of obstructive events associated with reduced respiratory effort but it may also present as a chaotic mixture of events of different kinds (e.g. obstructive apneas, central apneas, hypopneas) with no visually discernable pattern.

For several decades it has been possible to describe the necessary conditions for respiratory stability in mathematical terms. The analytical framework is identical to that used in classical process control theory for predicting the stability of a closed-loop negative feedback control system. While these systems are able stably to control very complex and sensitive processes if correctly tuned, certain categories of problems are known to cause instability and oscillating control that render the process useless or worse. In general, these problems are caused by an excessive sensitivity or "closed-loop gain" in the control loop and timing problems, where an excessive time delay is encountered in measuring the results of the process and taking the appropriate corrective action. These are the same problems that sufferers from unstable sleeping respiration often exhibit.

It is well-established that the underlying cause of instability in the chemical control of respiration is usually excessive gain or sensitivity of one of the blood gas sensors, namely the peripheral chemoreceptor. The peripheral chemoreceptor is located within the carotid artery and directly samples arterial blood for oxygen and $CO_2$ content. The chemoreceptor is sensing the concentration of $H^+$ ions in the blood, which is a proxy for $CO_2$ content in the arterial blood over a short period of time. The sensing becomes disordered and sends signals to the respiratory centers in the brain that tend to overestimate changes in blood gases, specifically, $CO_2$. Even though the cause of the disordered sensing is unknown, it is common in various diseases, e.g., heart failure. It is difficult to correct the above disordered sensing using current medical technology. Further, problems with blood circulation prolong the time delay in reporting changes in blood gases, which adds to the problem of instability in the patient's respiratory control loop.

Given that increased closed-loop gain in the respiratory control feedback loop resulting in unstable respiration is usually due either to excessively sensitive $CO_2$ sensors or impaired blood circulation, a number of therapeutic strategies have been attempted. Most existing therapies have various drawbacks.

Current therapeutic methods for restoring sleeping respiratory instability have the following problems:
1. They are complicated.
2. They are costly.
3. They are inefficient in that they may reduce one aspect of the closed-loop respiratory control gain while increasing its other aspects. Further, they may fail to reliably reinstate conditions for stability.
4. They fail to enable a clinician to specify a target blood $CO_2$ range to be maintained during therapy where patients are currently hypocapnic.
5. They reduce an amount of oxygen available for breathing, necessitating an addition of supplemental oxygen in order to restore normal level of blood oxygen.
6. They fail rapidly to excrete $CO_2$ under extraordinary circumstances, such as, after a prolonged obstructive apnea event.
7. They fail to respond immediately on a breath-by-breath basis to unstable respiratory patterns and rely on multi-breath pattern-recognition algorithms.
8. They relay on a single fixed estimate of respiratory requirements during the course of treatment and are not configured to adapt to variation in respiratory requirements.
9. They rely on expensive electronic equipment.

Current methods are also unable to permit modeling of the relationship between the rate ventilation of the patient and the rate of $CO_2$ excretion in a non-linear fashion, including imposition of multiple distinct steps that permit "clamping" of respiration by maintaining $CO_2$ excretion within a defined range under most conditions.

The system and method capable of controlling breathing of a patient by maintaining certain levels of $CO_2$ in the patient's blood, while maintaining or improving blood oxygenation, described herein provide a solution to these problems.

The present invention also provides a way to substantially eliminate "deadspace gain". This issue is present in some conventional breathing systems.

Unstable breathing patterns consist of alternating hyperventilation and hypoventilation or apnea. During hyperventilation, there is rapid "blow-off" of $CO_2$ that causes a steep drop in arterial $CO_2$ that initiates an epoch of hypoventilation or even apnea when the arterial blood reaches the peripheral chemoreceptor and the brain detects an abnormally low level of blood $CO_2$. During the hypoventilation, $CO_2$ accumulates rapidly and again initiates an epoch of hyperventilation. This pattern can be repeated indefinitely.

Ideally, the lungs should be made to be less efficient during hyperventilation in order to resist the $CO_2$ blow-off. One of the ways to do this, is to make the patient inhale a high percentage of $CO_2$ in inspired air, which will interfere with gas exchange in the lungs and therefore exhibit excessive excretion of $CO_2$. Likewise, the lungs should be maximally efficient during hypoventilation in order to limit the accumulation of $CO_2$. Thus, inhaled $CO_2$ is optimally zero during hypoventilation. Any design can be characterized in terms of its ability to exert a stabilizing influence by feeding the patient high concentrations of inspired $CO_2$ during hyperventilation and none during hypoventilation.

Figure 13:
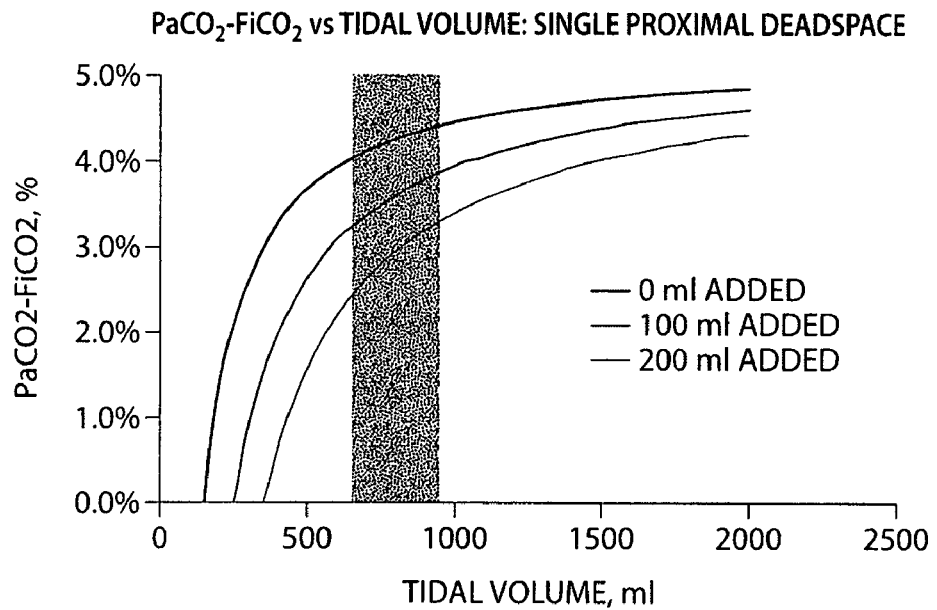
FIGS. 13-15 is a series of tracings indicating deadspace gain in conventional breathing systems.
Figure 14:
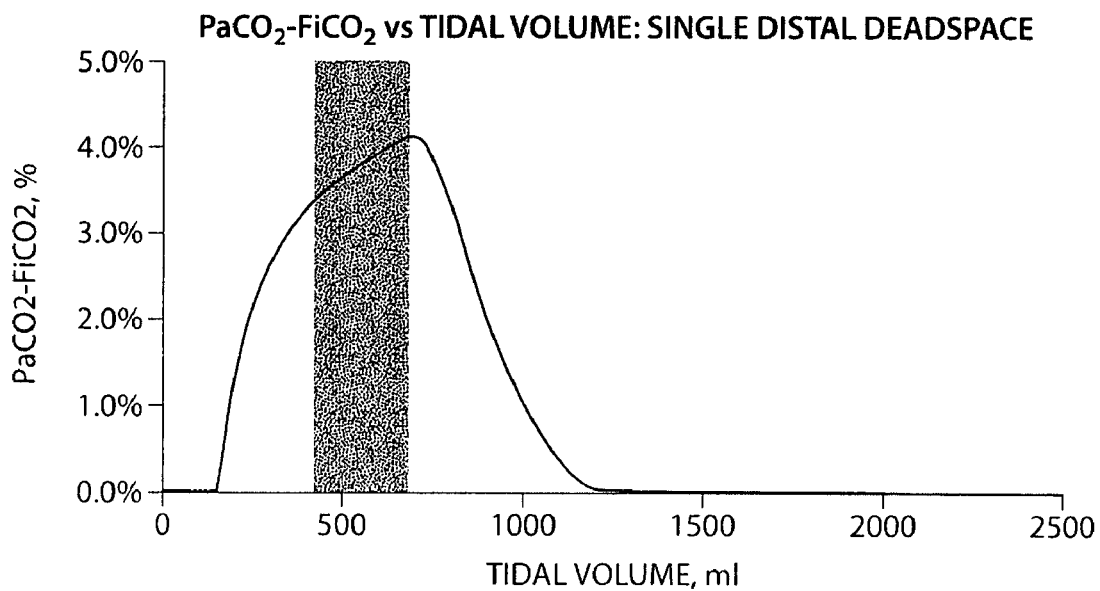
Figure 15:
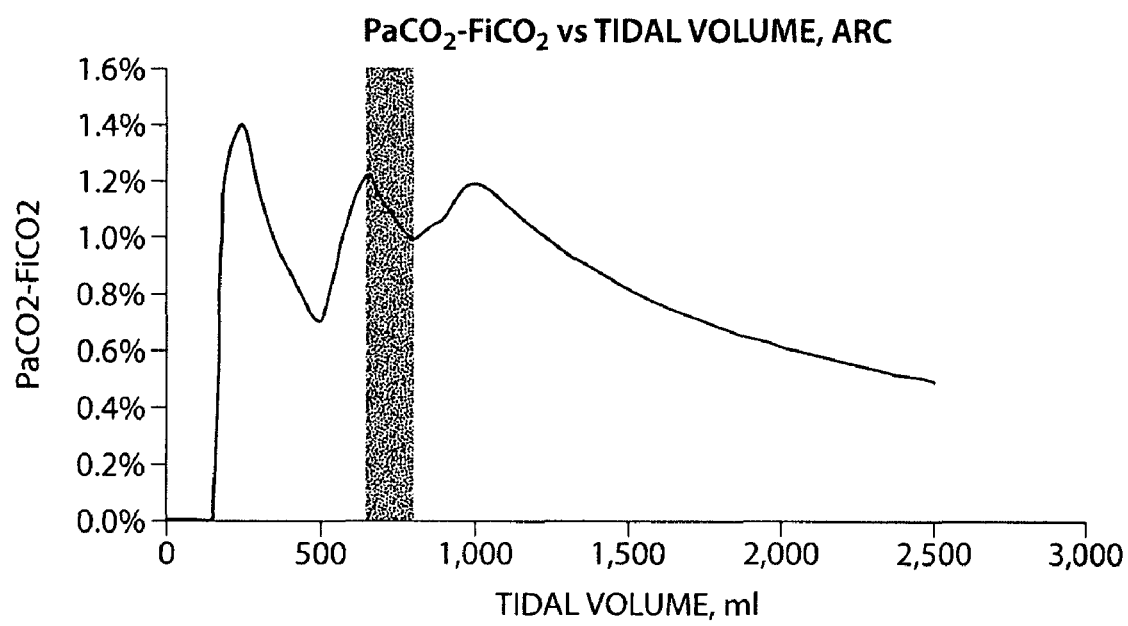

Unfortunately, the conventional deadspace systems tend to do the opposite. As tidal volume increases, the concentration of $CO_2$ in inspired air decreases, thus, actually promoting instability. FIGS. 13-15 illustrate that during normal breathing the deadspace gains of both proximal single deadspace design and distal single deadspace design are quite high. Single proximal deadspace systems interpose a single deadspace volume between a sealed patient interface and a single orifice configured to be large enough to permit flow through the orifice sufficient to wash out all exhaled gases that exceed the volume of the single deadspace. Such devices are then further connected to an air supply device via a typical respiratory conduit. Single distal deadspace systems are configured with a single orifice substantially on or near the patient interface and with a single conduit comprising the entire deadspace acting as a coupling to the air supply device. The single orifice is configured to permit a certain maximum amount of a gas to be excreted from the device and to cause substantial re-breathing of any additional exhaled gas. High deadspace gain is signified by a steep positive slope of the function in the shaded zone. The shaded zone represents a range of normal breathing while using the device.

Further features and advantages of the invention, as well as the structure and operation of various embodiments of the invention, are described in detail below with reference to the accompanying drawings. The invention is not limited to the specific embodiments described herein. Such embodiments are presented herein for illustrative purposes only. Additional embodiments will be apparent to persons skilled in the relevant art(s) based on the teachings contained herein.

While the present invention is described herein with reference to illustrative embodiments for particular applications, the invention is not limited thereto. Those skilled in the art with access to the teachings provided herein will recognize additional modifications, applications, and embodiments within the scope thereof and additional fields in which the present invention would be of significant utility.

Regulation of Blood Gas Levels

Methods and systems for controlling breathing of a patient are described herein. The methods and systems use a combination of multiple deadspace volumes and valves to control $CO_2$ levels in a patient's blood and, thereby, control breathing of the patient. The device of the therapeutic system controls a relationship between the rate of ventilation (i.e., total minute volume, $\dot{v}_E$) and the rate of $CO_2$ excretion ($\dot{v}_{CO_2}$) while permitting extensive modeling of this relationship in a non-linear, discontinuous fashion (See, FIG. 3 discussion below). This system allows a clinician to define a level of arterial blood $CO_2$ to be maintained during therapy as well as to place strong limits on both hyperventilation and hypoventilation. Under certain circumstances, the present invention can increase blood oxygenation without the use of supplemental oxygen.

The system provides an interaction between multiple discreet deadspace volumes and multiple ventilation orifices of either fixed (precisely-defined) or variable size, where the volumes and orifices can be organized in a specific pattern. Such interaction offers a possibility of defining a wide spectrum of relationships between the rate of ventilation and the rate of $CO_2$ excretion by the patient when used in conjunction with a ventilatory assist device such as a Continuous Positive Airway Pressure ("CPAP") machine, which is set to a predetermined pressure. In an alternate embodiment, a ventilatory assist device is not used and the same effect is achieved using a simple device into which the patient breathes.

A respiratory conduit, which is placed between a patient interface device (e.g., a sealed CPAP mask) and the CPAP machine (or any other air supply device), has a cylindrical shape. Ventilation orifices are placed in line with the conduit to provide outflow of $CO_2$ that is exhaled by the patient. The lengths of conduit lying between each ventilation orifice represent a distinct deadspace or quasi-deadspace volume. As air containing $CO_2$ is expelled from the patient's lungs into the respiratory conduit, a pressure generated by the CPAP machine causes at least some of the air and $CO_2$ contained in such air to flow out of the various orifices in a specific pattern. The pattern depends on the volume of each of patient's breaths or tidal volume ($V_T$) and the frequency of breathing, or respiration rate. Each breath consists of an expiratory interval and an inspiratory interval. Once the expiratory interval is over, inspiration commences and most or all of the remaining $CO_2$ in the conduit is re-breathed by the patient. Depending on the volume of each deadspace and the size of each ventilatory orifice, the curve describing a relationship between the rate of ventilation and the rate of $CO_2$ excretion has an arbitrary number of inflection points defining line or curve segments (See, FIG. 3), each with a different slope and length.

The above system permits extensive modeling of the relationship between a patient's breathing (i.e., ventilation) and excretion of $CO_2$. Using conventional computer simulation techniques, the sizes of orifices, volumes, and/or configuration of the two are specified to establish a relationship that serves to return the respiratory control feedback loop to a stable operation. Since during the interval prior to falling asleep, $CO_2$ production may be high relative to the levels anticipated to prevail during sleep, an auxiliary ventilation valve is fitted that permits the patient to increase airflow through the device until comfortably resting in bed.

Figure 1A:
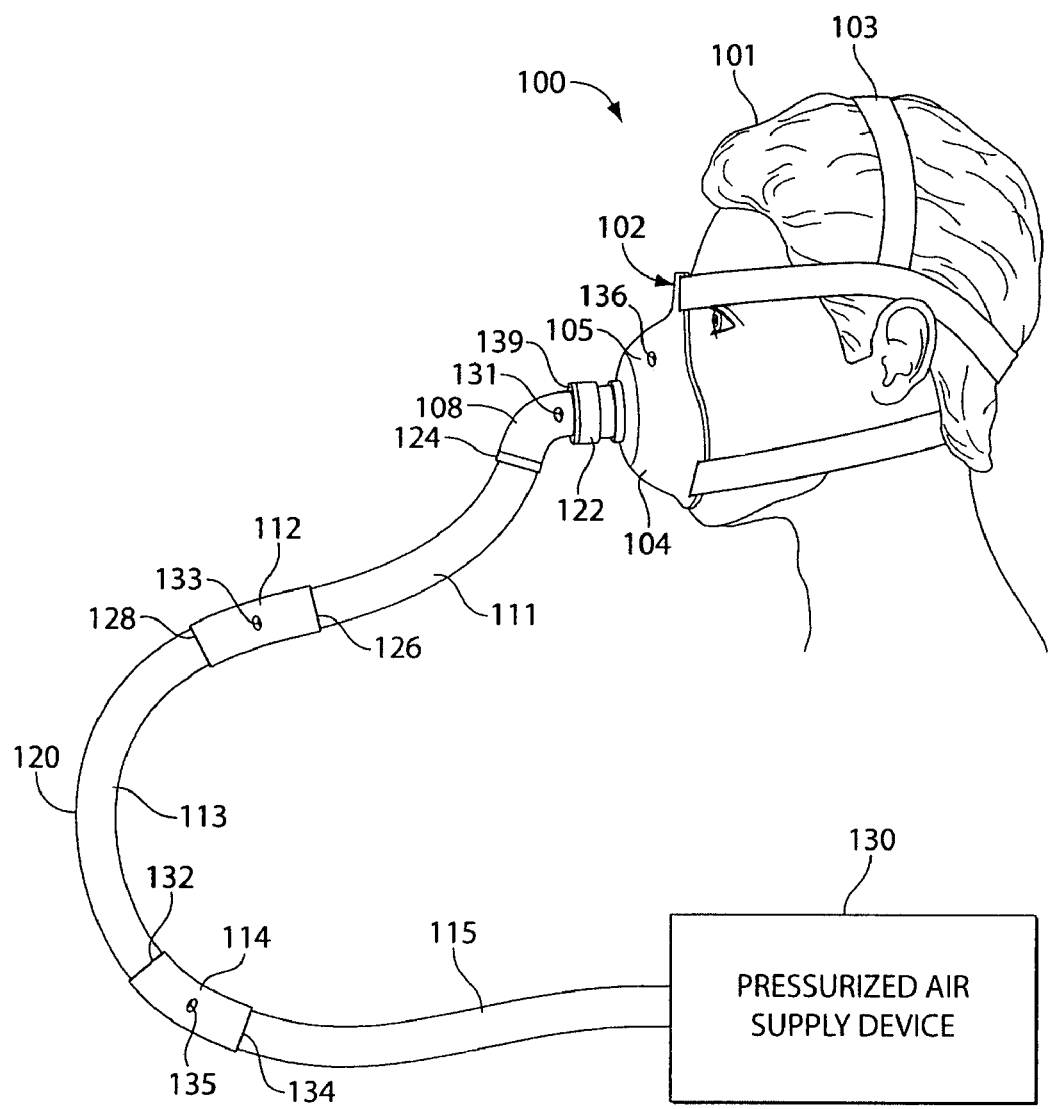
FIG. 1A is an illustration showing an exemplary system for controlling breathing of a patient, according to the present invention.
Figure 1B:
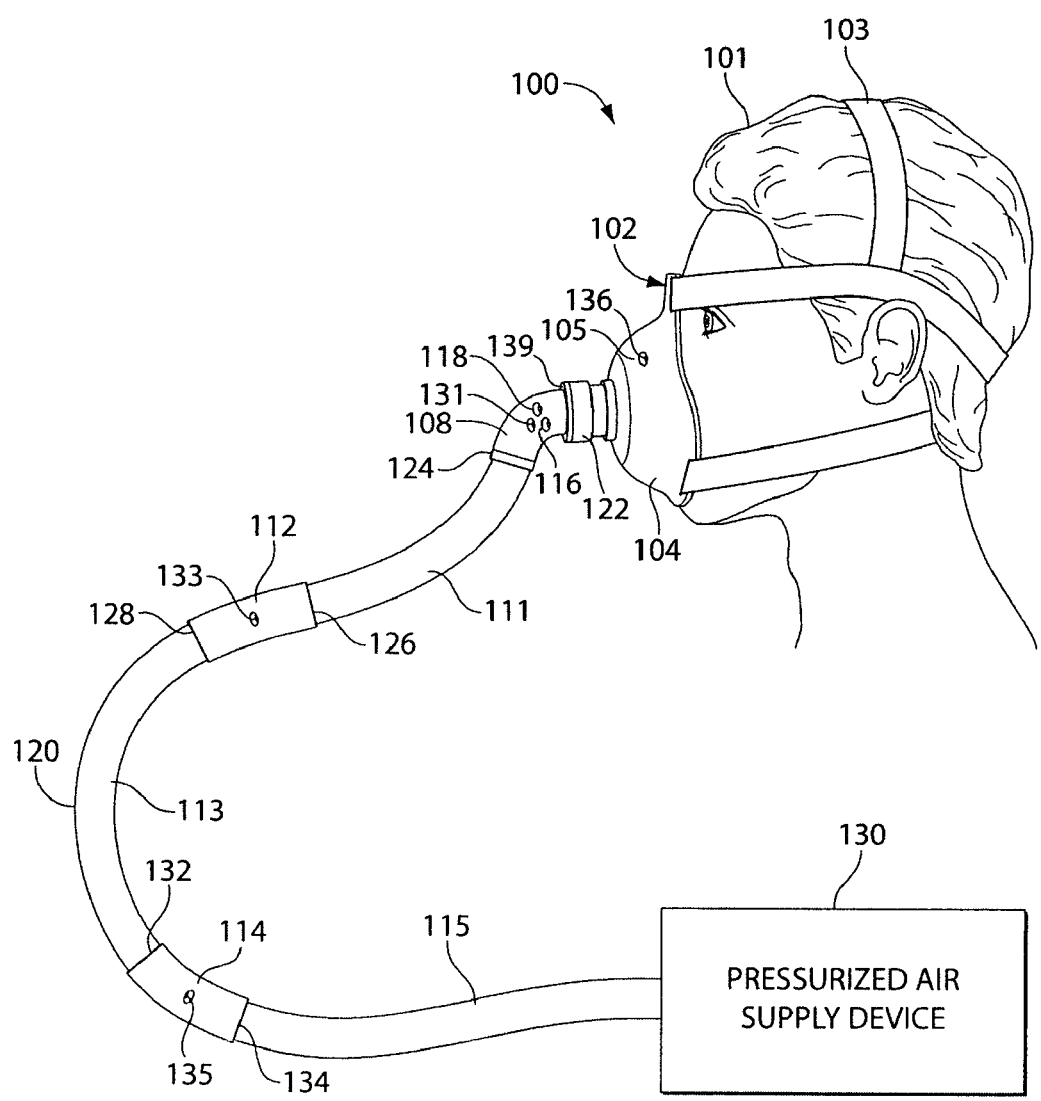
FIG. 1B is another illustration showing an exemplary system for controlling breathing of a patient, according to the present invention.

FIGS. 1A and 1B illustrate an exemplary system 100 for controlling breathing of a patient 101. Referring to FIG. 1A, the system 100 includes a respiratory conduit or a mixing device 120 configured to be coupled to mask and headgear assembly 102 and to a pressurized air supply device or CPAP device 130. The mask and headgear assembly 102 includes multiple straps 103 and a mask 104. The multiple straps 103 secure the mask 104 to the face of patient 101 so that there is a substantially sealed connection between the mask and the patient's breathing airway (e.g., nose or mouth). The sealed interface or connection prevents uncontrolled leakage of air or gases from openings that may occur between the patient's face and the mask. In the exemplary embodiment of FIG. 1A, one or a plurality of straps 103 are placed over upper and lower portions of the patient's head. As understood by one of ordinary skill in the art, other ways of securing the mask 104 to the patient 101 are encompassed herein. A pressurized and/or non-pressurized gaseous substance (including air, gas, etc.) generating device, e.g., the CPAP device 130, can be used with the therapeutic breathing system.

The mask 104 is a sealed orofacial non-invasive ventilation mask. For example, the mask 104 can be a Mirage NV Full Face Mask with adjustable VELCRO® strap headgear, as manufactured by ResMed Corp., Poway, Calif. A full-face mask can be used to cover both the nose and the mouth. This design eliminates mouth leak, permitting therapy for patients who breathe through the mouth and/or the nose. As can be understood by one of ordinary skill in the art, other types of masks can be used, such as a nasal mask, an oral mask, an orofacial mask, a nasal prong device, an intra-oral device, an endotracheal tube, or any other device.

The mask 104 includes a mask valve 105. The mask valve 105 can be a female Luer fitting that includes an orifice 136 and that attaches to one of the existing Luer ports on the mask 104. The orifice 136 can be drilled, punctured, or created by any other methods. The mask valve 105, through orifice 136, allows escape of gas (e.g., $CO_2$) exhaled by the patient.

Alternatively, the mask 104 does not include the mask valve 105. Instead, a first valve 108 is placed on the mixing device 120, substantially adjacent to the mask 104. In one example, the orifice 136 has a fixed size. This design allows a certain volume of air to escape from the mask valve 105 per unit of time. In another example, the orifice 136 has a variable size, which can be altered depending on the amount of air intended to be allowed to escape from the mask valve 105. In one example, the orifice 136 permits air flow of 0.5-6 liters per minute, when the mask is pressurized by the CPAP machine 130 at a specific pressure. This pressure can be equal to the patient's CPAP pressure prescription.

Referring back to FIG. 1A, the mixing device 120 includes a first valve 108, a first volume 111, a second valve 112, a second volume 113, a third valve 114, and a connector volume 115. The first valve 108 includes an orifice 131. The second valve 112 includes an orifice 133. The third valve 114 includes an orifice 135. As can be understood by one having ordinary skill in the relevant art, the mask valve 105 can be the first valve 108. The mask valve 105 can be included or absent from the mask 104. Also, the first valve 108 can be placed on the mask 104 instead of the fitting 139.

As shown in FIG. 1A, a fitting 139 incorporates the first valve 108. The fitting 139 is coupled to the mask 104 and the first volume 111. The second valve 112 is coupled to the first volume 111 and the second volume 113. The third valve 114 is coupled to the second volume 113 and connector volume 115. The connector volume 115 is coupled to the pressurized air/gas generating device 130.

The fitting 139 further includes fittings 122 and 124 through which it is coupled to the mask 104 and first volume 111, respectively. The fittings 122, 124 can be standard type fittings having 22 mm outside diameter ("o.d."). To allow proper connection to the fitting 139, the first volume 111 can be a standard 22 mm inside diameter ("i.d.") respiratory hose.

Further, the fittings 122, 124 can be of a swivel type to permit rotation of the fitting 139 to accommodate various positions and orientations of the mixing device 120 and provide substantially leak proof connection. Otherwise, fitting 139 can be a straight fitting or a bent fitting, for example a fitting with two 22 mm o.d. ends and a 90-degree bend. The first valve 108 provides an air flow of 0.5 to 6 liters per minute when the system 100 is pressurized by the CPAP machine 130 at a given pressure equal to the patient's CPAP pressure prescription. Fittings 126, 128 (coupling second valve 112 to first volume 111 and second volume 113, respectively) and fittings 132, 134 (coupling third valve 114 to second volume 113 and connector volume 115, respectively) can be similar to fittings 122, 124.

The first volume 111 can be a standard 22 mm i.d. respiratory hose and can have an internal volume of 100-400 ml depending on the desired increase in the patients' arterial $CO_2$. The hose can be a conventional hose with rubber cuffs as used with CPAP machines; it can be a corrugated disposable respiratory hose, or it can be any other hose appropriate for connecting mask 104 to a fitting 126.

As stated above, the second valve 112 includes a straight connector incorporating the orifice 133 that can have a fixed size. Alternatively, the orifice 133 has a variable size. This connector can be plastic and have 22 mm o.d. ends suitable for connection to the first volume 111 and second volume 113. Further, the orifice 133 location in the connector is such that it is not obstructed by lying on a surface (e.g., a bed). A groove in the fitting containing the second valve 112 can be created to prevent any obstructions. The orifice 133 permits an airflow of 3-8 liters per minute when it is pressurized by the CPAP machine 130 at a given pressure equal to the patient's CPAP pressure prescription.

The second volume 113 is substantially identical in type to the first volume 111. The second volume 113 can have a total volume of 100-400 ml.

The third valve 114 incorporates the orifice 135, which can be variable or fixed. The third valve 114 can be a straight connector, as shown in FIG. 1A. The connector can be plastic and have 22 mm o.d. ends suitable for connection to the first volume 113 and connector volume 115. The orifice 135 location in the mixing device 120 is such that it is not obstructed by lying on a surface (e.g., a bed). A groove in the fitting containing the third valve 114 can be created to prevent any obstructions. The orifice 135 permits an airflow of 15-30 liters per minute when it is pressurized by the CPAP machine 130 at a given pressure that is equal to the patient's CPAP pressure prescription.

The connector volume 115 can be substantially identical in type to the first volume 111 and second volume 113. The length of the connector volume 115 can be set to accommodate placement of the CPAP machine 130 in relation to the patient 101.

Each one of the orifices 131 (or alternatively 136), 133, and 135 is configured to allow escape of air at a specific rate when the pressurized air supply device 130 is operated at a specific pressure. Depending on the concentration of gas in the air flowing through each of the orifices, the gas will be escaping through each orifice at a specific rate. The orifices can be fixed, variable, or a combination of fixed and variable sized orifices can be used. As can be understood by one having ordinary skill in the art, varying locations and/or numbers of fixed and variable orifices can be used as desired. This allows a predetermined amount of air and gas (depending on the concentration of the gas in such air) to escape from the orifices in case of fixed orifices' sizes or a variable amount of gas to escape from the orifices in case of variable orifices' sizes. Further, in case of variable orifices, their sizes can be manually or dynamically controlled. When orifice sizes are manually controlled, a patient, a clinician, or someone else can control the size of the orifice and, thus, the amount of gas allowed to escape from the orifice. When orifice sizes are automatically controlled, their sizes can be adjusted automatically based on an amount of gas exhaled by the patient, amount of gas escaping from each specific orifice, amount of gas contained in the volume connectors 111 and 113, patient physical parameters (such as blood pressure, body mass, age, etc.) and/or other factors.

The sizes of orifices 131, 133, 135 and three volumes 111, 113, 115 can be preliminary determined using an algorithm based on patient's estimated high and low $\dot{v}_{CO_2}$ (rate of production of $CO_2$ in ml per minute) as directly measured during sleep. Alternatively, the patient's estimated high and low $\dot{v}_{CO_2}$ can be derived from patient's body mass or any other physiological or demographic variable or combination of variable. The sizes of volumes and orifices are adjusted during a polysomnographic study in a clinic, hospital, laboratory, or any other facility that is equipped with $CO_2$ monitoring equipment. Based on the adjustment, a final combination of orifices and volumes is determined. This combination establishes a first respiratory plateau (See, FIG. 3, segment 308) at or below a value of $\dot{v}_{CO_2}$ equal to the minimum estimated $CO_2$ production per minute expected to occur during sleep and a second respiratory plateau (See, FIG. 3, segment 310) at or above a value of $\dot{v}_{CO_2}$ equal to the maximum estimated $CO_2$ production per minute expected to occur during sleep.

The respiratory conduit 120 is rotatably coupled to the mask 104 and the CPAP device 130. This arrangement allows the conduit 120 to rotate if the patient turns during sleep. As can be understood by one of ordinary skill in the art, the rotatable connection can be sealed to prevent any leaks during operation of system 100.

Referring to FIG. 1B, the conduit 120 includes an anti-asphyxiation valve 118 and any number of auxiliary valves 116 that can assist a patient during breathing. In the FIG. 1B example, the anti-asphyxiation valve 118 and the auxiliary valve 116 are placed in the fitting 139.

The auxiliary valve 116, when opened, provides a flow of air through the mixing device 120 sufficient to provide substantial washout of the exhaled $CO_2$ from the mixing device 120. In one example, the patient 101 can operate the auxiliary valve 116 in order to provide $CO_2$ washout until patient 101 is resting comfortably. The auxiliary valve 116 can be closed manually by the patient 101 or automatically after a certain period of time elapsed.

The anti-asphyxiation valve 118 opens when the operating pressure of the CPAP machine 130 falls below a predefined value (i.e., CPAP machine 130 fails to provide adequate pressure). When the latter occurs, the anti-asphyxiation valve 118 opens and allows the patient 101 to breathe ambient air through the valve 118. Hence, the valve 118 prevents asphyxiation of the patient in the event of failure of the CPAP machine 130.

Additionally, the mixing device 120 includes a water condensation collection device that collects moisture from the patient's breaths. This prevents undesirable accumulation of moisture within the mixing device 120.

For example, it may be determined that a male patient with a body mass of 100 kg and a CPAP prescription of 15 cm $H_2O$ may require the following configuration of orifices and volumes:

| | |
|---|---|
| Orifice 131 | 3 liters per minute |
| First volume 113 | 350 ml |
| Orifice 133 | 5 liters per minute |
| Second volume 115 | 400 ml |
| Orifice 135 | 22 liters per minute |

Figure 2A:
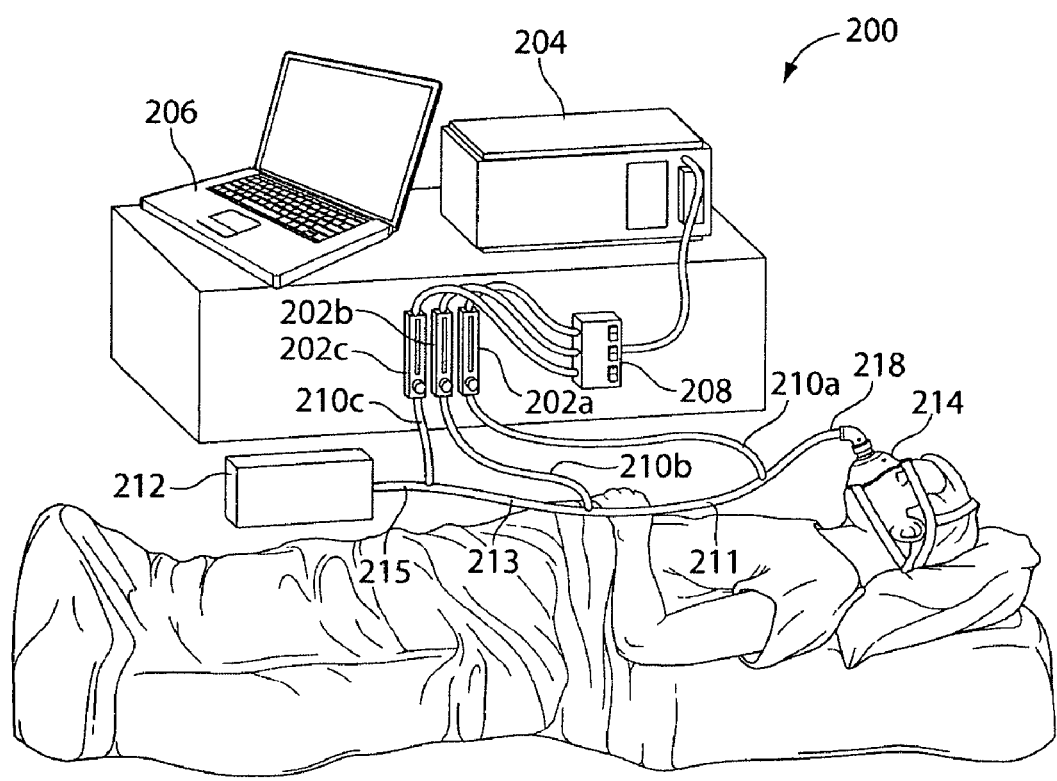
FIG. 2A is an illustration showing exemplary clinical equipment set up using methods and systems for controlling breathing of a patient, according to the present invention.

FIG. 2A illustrates an exemplary set up 200 for a polysomnographic and/or titration study of a patient. The set up 200 includes a $CO_2$ monitor 204, a computing device 206, variable area flow meters 202 (a, b, c) having needle valve controls, a CPAP machine 212, a switchable manifold 208, tubing 210 (a, b, c), a conduit 218, and an orofacial mask 214.

The mask 214 is similar to 104 shown in FIGS. 1A and 1B. The CPAP machine 212 is similar to the CPAP machine 130. Also, the conduit 218 is similar to the mixing device 120. The conduit 218 connects mask 214 and CPAP machine 212. The conduit 218 is also connected to tubing 210 (a, b, c). The conduit 218 includes a first volume 211, a second volume 213, and a connector volume 215, which are similar to the volumes 111, 113, and 115, respectively. The tubing 210a connects orifice 131 (not shown in FIG. 2A) a flow meter 202a. The tubing 210b connects orifice 133 (not shown in FIG. 2A) to a flow meter 202b. The tubing 210c connects orifice 135 (not shown in FIG. 2A) to a flow meter 202c. The tubing 210 (a, b, c) can be 3/8 inch i.d. Tygon tubing. The tubing 210 (a, b, c) can be glued, cemented, or otherwise securely fastened to the orifices 131, 133, 135 and flow meters 202 (a, b, c), respectively.

Figure 2B:
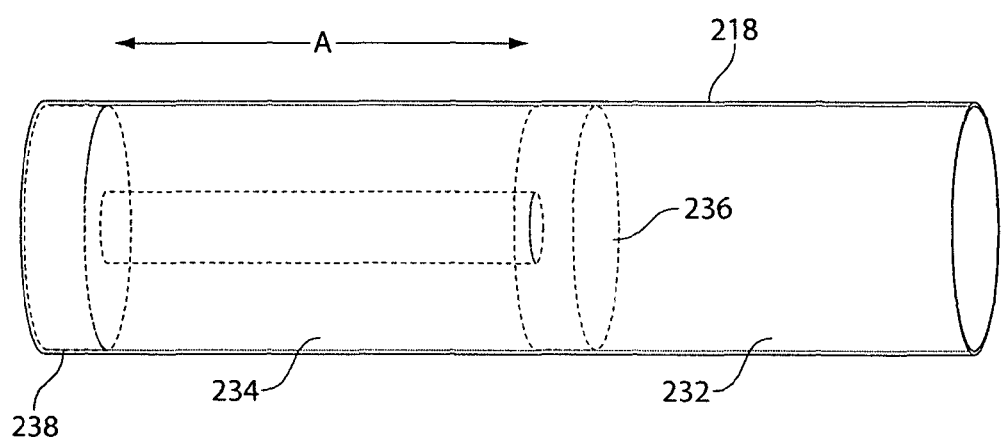
FIG. 2B is an illustration of a portion of breathing conduit shown in FIGS. 1A-2A.

Further, the conduit 218 is configured to vary volumes 213 and 215 using movable pistons or cylinders (shown in FIG. 2B) located inside the volumes 213 and 215. The cylinders can be sealed using o-ring clamps (shown in FIG. 2B). FIG. 2B illustrates a portion of the conduit 218 having a cylinder/piston 236 placed in the conduit's interior 234. The cylinder/piston 236 is able to move back and forth as shown by the bi-directional arrow A. The movement increases or decreases deadspace volume 232. The cylinder/piston 236 is secured by an o-ring clamp 238. This cylinder/piston 236 arrangement can be placed in either or all volumes 211, 213, and 215. The volumes can also include graduation scales (not shown in FIGS. 2A, 2B) to adjust the deadspace volume 232 to a specific value.

Referring back to FIG. 2A, the output sides of the flow meters 202 (a, b, c) are coupled to switchable manifold 208, which allows measurement of $CO_2$ content in the air flowing from any one of or a combination of the variable flow meters 202 (a, b, c) by the monitor 204. The monitor 204 is connected to the computing device 206, which collects the data. The data is used to adjust the rates of airflow through each of the flow meters 202 and the sizes of the volumes, as described with respect to FIGS. 1A, 1B and 3-9.

Method of Treatment and Titration of a Patient

Initially, a nightly $CO_2$ excretory profile of a patient during sleep is determined. This profile is determined by measuring a total amount of $CO_2$ production by the patient during a diagnostic overnight polysomnographic study. Such profile contains information about high, low and mean levels of $CO_2$ production during sleep. Prior to a trial fitting of the device (See, FIGS. 1A-2) on a patient, the collected data along with other patient physiological data and desired therapeutic results are used to generate a simulation model, which provides a best estimate of a configuration of volumes and orifices to be used during treatment. During a subsequent polysomnographic titration study the device is fitted on the patient, an initial CPAP pressure is selected and an actual $CO_2$ flow through each of the orifices is measured at the predetermined air flow rate. The orifice sizes are adjusted (either manually or automatically) so that the $CO_2$ flow through or escape from each orifice equals a desired value depending on an intended relationship to the patient's $CO_2$ excretory profile. The volumes' sizes are also adjusted (whether manually or automatically). This depends on whether patient's mean amount of arterial $CO_2$ diverges from the desired level. The adjustment of sizes can be done by physically substituting volume hoses of known size. Alternatively, a cylinder/piston arrangement (shown in FIG. 2B) can be inserted into each of the volumes to manually or automatically decrease or increase the interior spaces of the volumes based on the obtained data and desired values. In the event that it is necessary to change the starting CPAP pressure, the procedure of measuring and adjusting can be repeated to return to a specific desired result.

At the end of the titration study, a final configuration of CPAP pressure, volumes and airflow through each of orifices is recorded. A custom-built conduit/mixing device (as shown in FIGS. 1A-2B) can be manufactured according to these specifications and dispensed to a patient for use. As can be understood by one having ordinary skill in the art, various configurations of orifices and volumes are possible.

The device and therapeutic system is tailored to each individual patient. Initially, the patient is referred to an appropriate sleep diagnostic facility. In the facility, a clinician orders an evaluation of a patient for possible respiratory instability. Certain modifications and enhancements are optionally made to the usual overnight polysomnographic study, described above. These modifications can include additions of end-tidal $CO_2$ monitoring and calibrated nasal pressure measurement. Alternatively, instead of nasal pressure, another highly accurate means of determining airflow through the patient's nose and mouth can be utilized, including wearing a respiratory mask with an attached flow sensor. The capnography ($CO_2$) waveform (See, FIG. 6) and flow signals are recorded throughout the night and stored in the polysomnographic recording system. As a result of the study, either in real time or a post-study process, a patient's minute $CO_2$ volume ($\dot{V}_{CO_2}$) versus time, i.e., a rate of $CO_2$ excretion during sleep, is derived by multiplying the sum of the rates of airflow through the orifices and the airflow meters and the percentage of $CO_2$ in the air, as measured by the end-tidal $CO_2$ monitor. The patient's $CO_2$ excretion profile is determined using a number of commercially available analytic packages, such as DASYlab, manufactured by National Instruments Corporation of Austin, Tex.

The interpreting clinician inspects the evolution of $\dot{v}_{CO_2}$ during the course of the night and determines the predicted low, mean, and high $\dot{v}_{CO_2}$ targets for which the device should be configured. The clinician also inspects the end-tidal $CO_2$ waveform itself to evaluate the evolution of arterial $CO_2$ and to determine to what degree the patient will require overall $CO_2$ support in order to reach a target mean arterial $CO_2$ level during the night. The clinician then again refers the patient for a titration study using the present invention.

Prior to the titration study, the polysomnographic technician will obtain certain demographic and physical information about the patient in order to establish a starting configuration. For example, age, sex, body mass, arterial $CO_2$ level, estimated CPAP prescription, and actual and target end-tidal $CO_2$ values are collected. This information is then used to make an estimate of a probable optimal configuration of orifices and volumes. Patient's age, sex and body mass are used to derive a probable low, mean, and high value for sleeping $\dot{v}_{CO_2}$ based on at least studies of multiple patients. Then, $\dot{v}_{CO_2}$ values are used to set target flow rates for the orifices and determine the size of the orifices based on flow rates through each orifice under pressure. The size of the first deadspace volume 111 is estimated based on the desired target end-tidal $CO_2$. Finally, a minimum size for the third orifice 115 is estimated. This permits a washout of any overflow $CO_2$.

After the study is completed, the patient can be provided with a home-use device that is similar to the system 100 shown in FIG. 1. Alternatively, the patient can be scheduled for treatment at a clinic using the system of present invention. The device is capable of the following exemplary functions:

(i) measuring an airflow through each ventilatory orifice 131, 133, 135 individually (conventional gauges can be used as variable area flowmeters or electronic flowmeters coupled to an input/output device, e.g., a computer, can be used to measure the airflow);

(ii) detecting $CO_2$ content in airstreams stemming from each orifice 131, 133, 135 and transmitting the collected content data to an input/output device, e.g., a computer;

(iii) adjusting airflow through (or escaping from) each of the orifices 131, 133, 135 using valves (the valves can be operated manually or automatically);

(iv) adjusting sizes of the two deadspace volumes by disconnecting and connecting hoses of various lengths (alternatively, variable volume devices can be incorporated, which permit altering the deadspace volumes without changing hoses; the variable volume devices can be nested cylinders sealed with o-rings that can slide in and out); and (v) computing and displaying a rate of flow of $CO_2$ through each of the orifices (this function can be performed by any computing device having an appropriate data acquisition peripheral device running on software, such as DASYLab, which permits acquisition of both the $CO_2$ and flow data channels; a suitable display can be used to permit a clinician to observe flow of $CO_2$ through each orifice as the volumes are adjusted).

Figure 8:
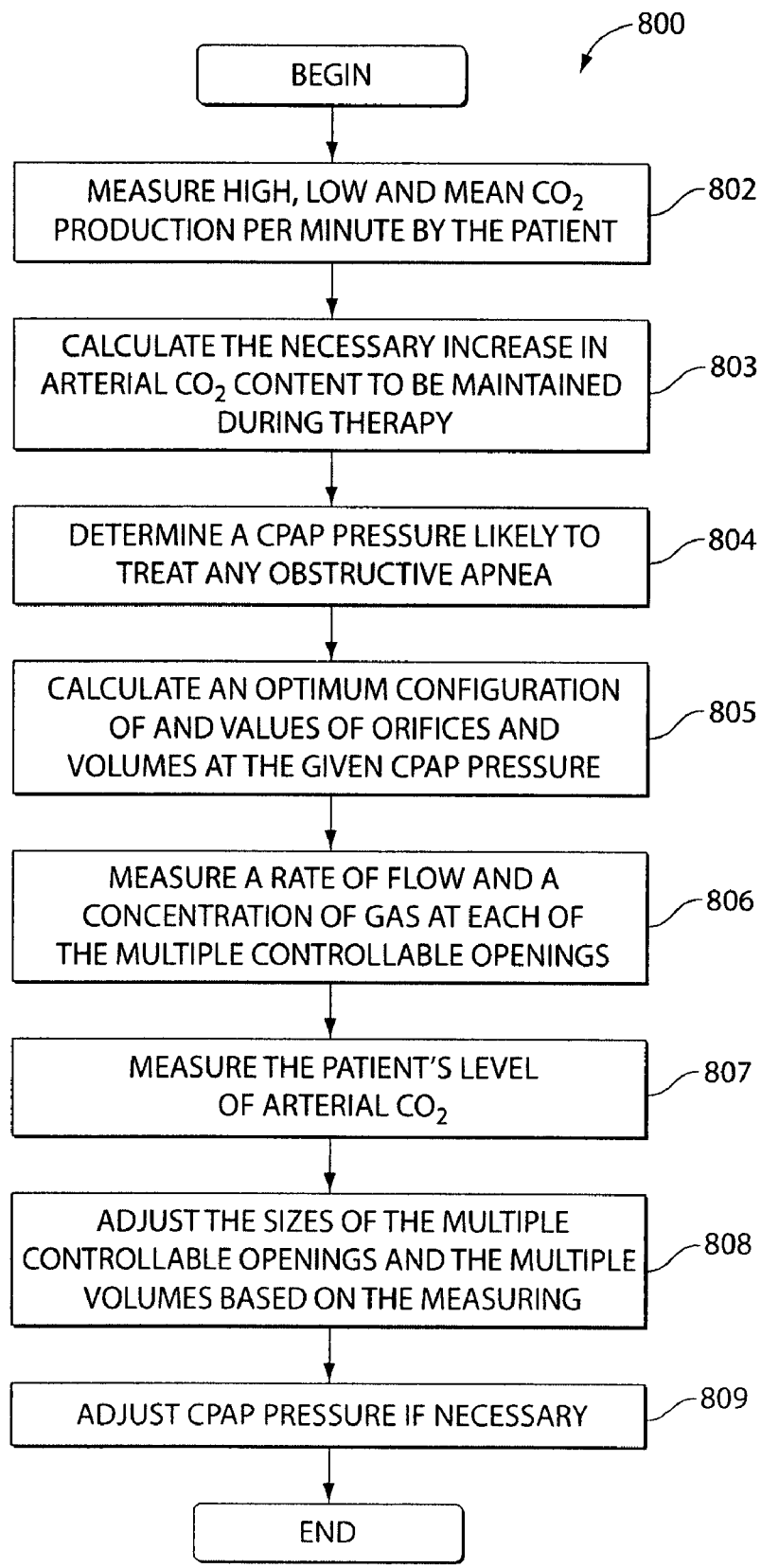
FIG. 8 is a flow chart illustrating an exemplary method for controlling breathing of a patient, according to the present invention.
Figure 9:
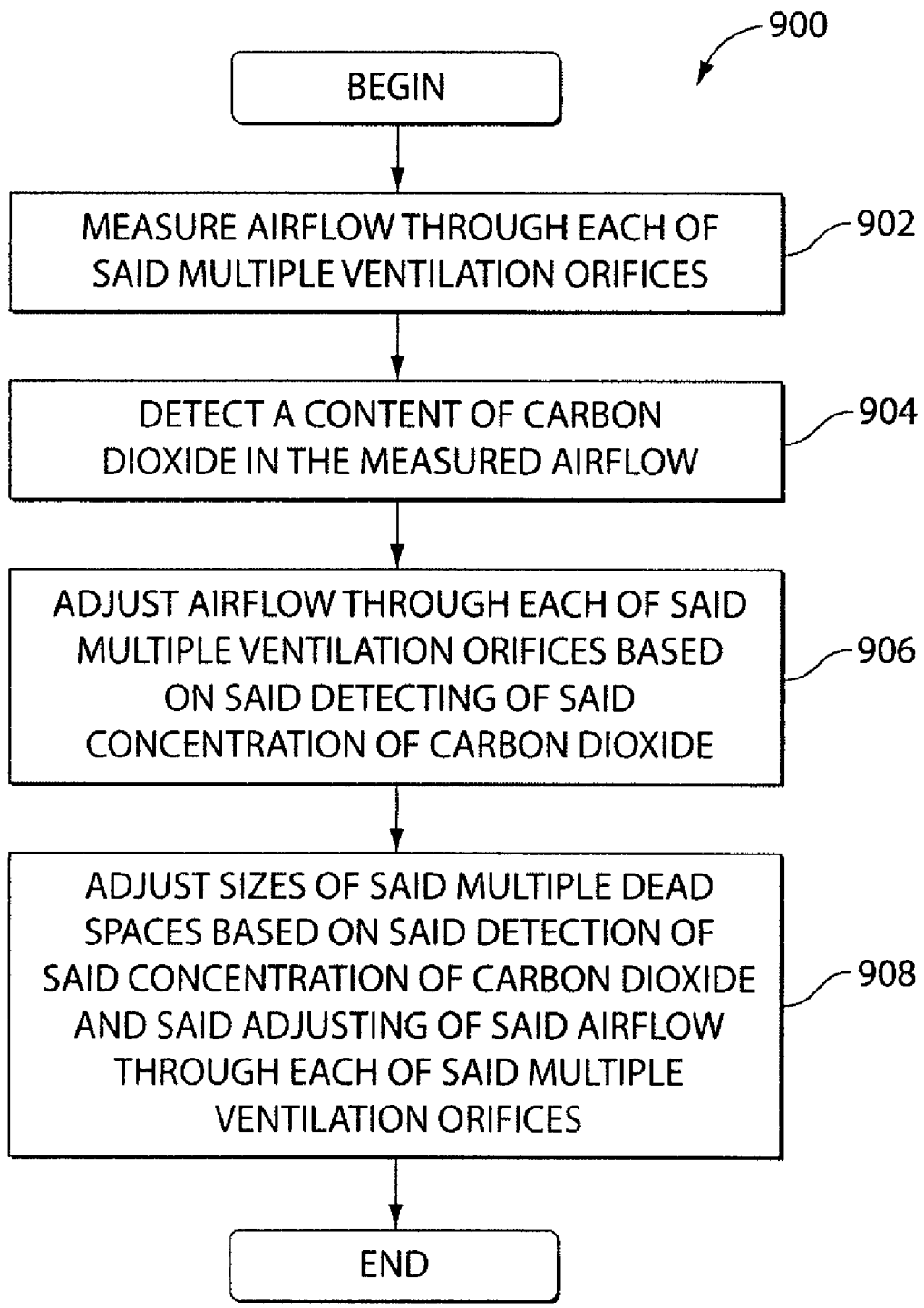
FIG. 9 is a flow chart illustrating an alternate embodiment of a method for controlling breathing of a patient, according to the present invention.

FIGS. 8 and 9 illustrate exemplary methods 800 and 900, respectively, of controlling breathing of a patient in accordance with the above discussion and using the systems shown in FIGS. 1A-2B. Referring to FIG. 8, method 800 begins with step 802. In step 802, the amount of $CO_2$ generated by the patient is determined (high, low and mean values of $CO_2$ production per minute by the patient are measured). Then, the processing proceeds to step 803, where the end-tidal $CO_2$ tracing for the night is inspected to determine the magnitude of a desired increase in the mean arterial $CO_2$ during therapy. In step 804, the optimum CPAP pressure likely to treat any existing obstructive apnea is determined. Then, in steps 805 and 806, a preliminary configuration of the system 100 is determined using the data gathered in steps 802-804. To configure the system, a computer simulation of the performance of the system under various assumptions can be used. Alternatively, empirically determined values for the orifices and volumes that are a function of the data gathered in steps 802 and 804 in addition to patient's physiological and/or demographic data can be used. In step 806, a rate of flow and concentration of gas at each of the multiple controllable openings is measured. In step 807, patient's arterial $CO_2$ level is measured. Then, in steps 808-809 the sizes of the orifices, volumes, and optionally CPAP pressure are adjusted. Steps 808-809 can be repeated until a specific configuration of orifices, volumes and CPAP pressure is reached.

Referring to FIG. 9, method 900 begins with step 902, where airflow through each of the multiple ventilation orifices 131, 133, 135 is measured. In step 904, the content of $CO_2$ in the airflow, measured in step 902, is determined. The method then proceeds to step 906. In step 906, the airflow is adjusted through each of the multiple ventilation orifices based on the detecting, performed in step 904. In step 908, the sizes of the deadspace volumes are adjusted also based on the detecting of step 904 as well as the adjustment of the multiple ventilation orifices performed in step 906.

As can be understood by one having ordinary skill in the art, the above methods can be applied in a laboratory setting, a hospital, a clinic, at patient's home, or any other facility.

Figure 3:
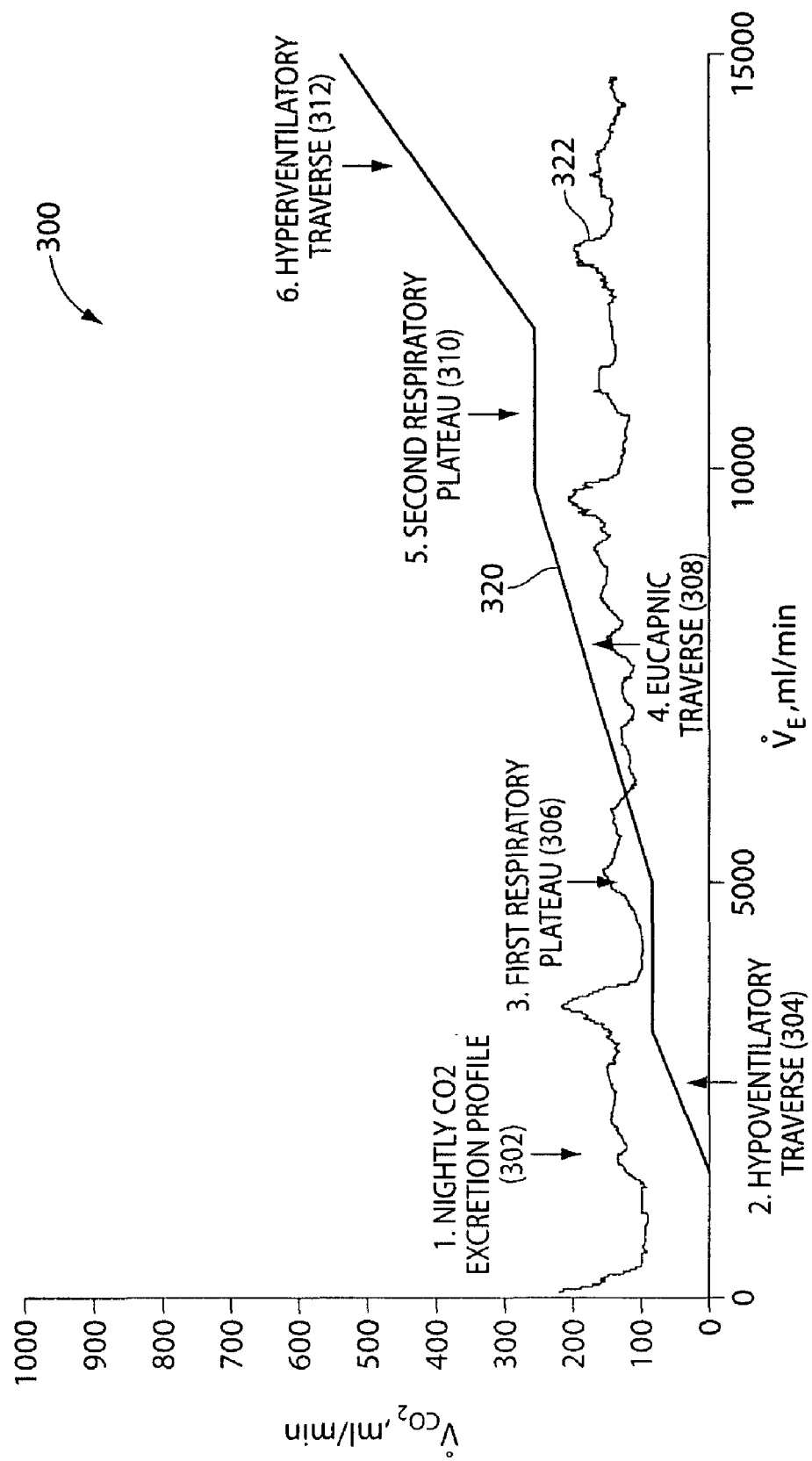
FIG. 3 is an exemplary graphical representation of a relationship between ventilation (i.e., the total volume of air exhaled and inhaled by the patient per minute) and $CO_2$ excretion by the patient using systems and methods for controlling breathing of a patient, according to the present invention, along with a tracing representing a rate of $CO_2$ production by the patient during a night.

FIG. 3 illustrates a relationship 300 between multiple deadspace volumes 111, 113, 115 and multiple orifices 131, 133, 135, which permits an extensive modeling of the rate of excretion of $CO_2$ ($\dot{v}_{CO_2}$) by the patient with respect to various rates of ventilation ($\dot{v}_E$). In an embodiment, the present invention includes two deadspace volumes 111 and 113 and three ventilation orifices 131, 133, 135 that cause various changes in the slope of FIG. 3.

Figure 4:
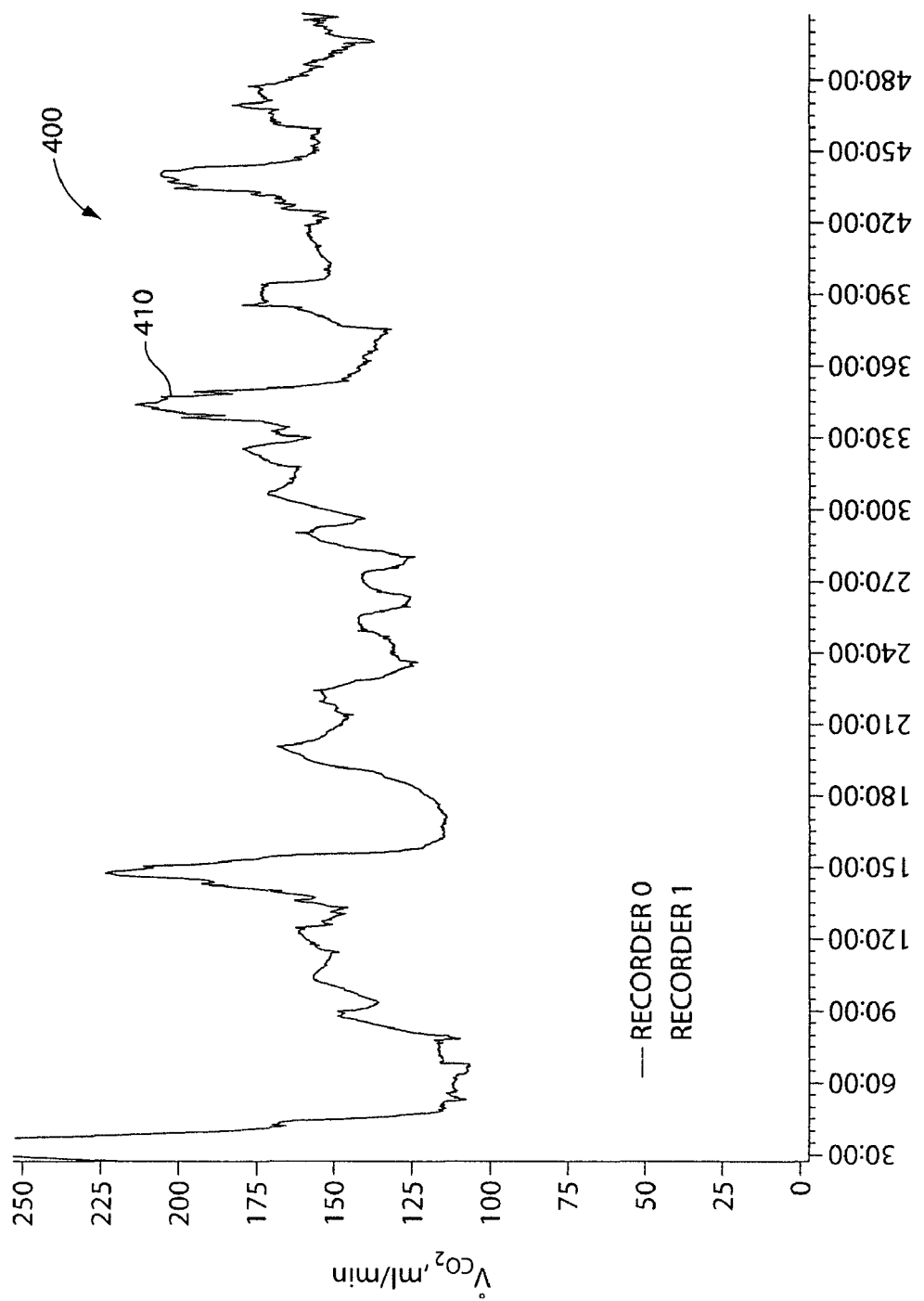
FIG. 4 is a graphical representation of a typical $CO_2$ excretion by the patient during a night.
Figure 5:
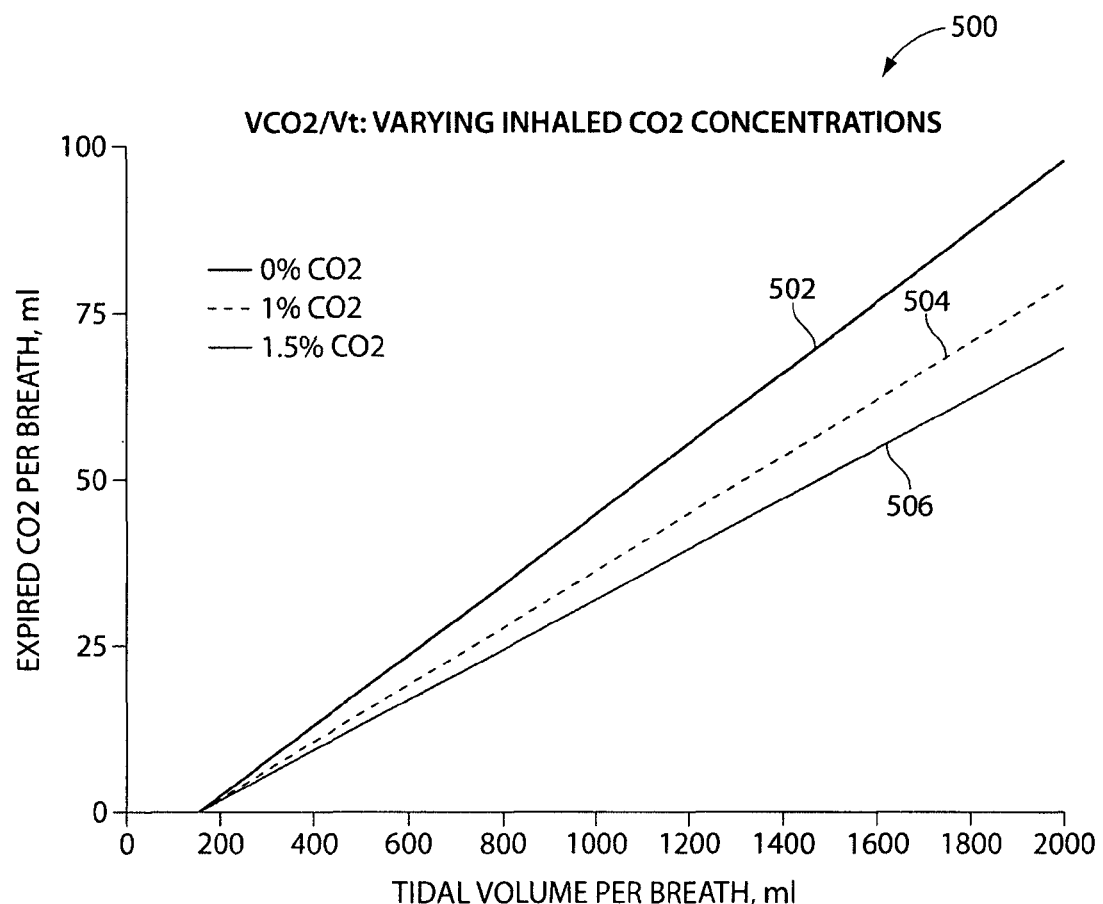
FIG. 5 is a graphical representation of a relationship between depth of breathing (i.e., tidal volume) and $CO_2$ excretion during a single breath by the patient using conventional methods and systems for controlling breathing a patient.

In FIG. 3, curve 302 represents a nightly $CO_2$ excretion profile of a patient which is overlaid on the plot to illustrate the range of likely $CO_2$ excretion rates by the patient. Referring to FIG. 4, the horizontal axis of the plot represents time in minutes and the vertical axis represents a rate of production of $CO_2$ by a patient per minute, as measure in milliliters per minute (ml/min). Referring back to FIG. 3, the horizontal axis represents patient's rate of ventilation ($\dot{v}_E$), measured in ml/min, and the vertical axis represents the rate of excretion of $CO_2$ ($\dot{v}_{CO_2}$) by the patient in ml/min when the present invention's system is used. A typical relationship between these two quantities, when the present invention's system is not used, is defined as follows:

$$\dot{v}_{CO_2} = (\dot{v}_E - \dot{v}_D) * (F_{ACO_2} - F_{ICO_2}) \qquad (1)$$

where $\dot{v}_D$ is equal to the sum of the physiological and artificially added volumes of deadspace multiplied by the respiratory frequency; $\dot{v}_E$ is equal to the total volume of air inspired and expired during each breath multiplied by the respiratory frequency, $F_{ACO_2}$ is the partial pressure of dissolved $CO_2$ in arterial blood divided by an ambient air pressure; $F_{ICO_2}$ is a fractional concentration of $CO_2$ in the air inspired by the patient. The function described in equation (1) is represented by a straight line that intersects a horizontal axis above zero.

Referring back to FIG. 3, the curve 320 describes a relationship between $\dot{v}_E$ and $\dot{v}_{CO_2}$, according to the present invention, and includes the following segments: hypoventilatory traverse segment 304, first respiratory plateau segment 306, eucapnic traverse segment 308, second respiratory plateau segment 310, and hyperventilatory traverse segment 312. Each segment has a specific slope and length defined by the number and size of deadspace volumes and orifices placed in the respiratory conduit as well as volume of $CO_2$ flowing through the deadspace volumes and orifices. Thus, the number of segments varies with the number of deadspace volumes and orifices in the conduit.

As shown in FIG. 3, the hypoventilatory traverse segment 304 is caused by the placement of the first orifice in the respiratory conduit. The slope of the segment illustrates a normal relationship between breathing and $CO_2$ excretion described in equation (1) until a saturation point is reached. The saturation point that corresponds to a maximum rate of $CO_2$ flow through the first orifice is represented as the junction of the segment 304 and segment 306.

This hypoventilatory traverse describes a relationship between ventilation and $CO_2$ excretion while the patient is hypoventilating. At values of $\dot{v}_{CO_2}$ below the estimated minimum sleeping level, the relationship between $\dot{v}_E$ and $\dot{v}_{CO_2}$ is substantially unchanged from the normal physiological relationship. One of the destabilizing elements in unstable respiratory syndromes is the rapid accumulation of blood $CO_2$ during epochs of hypoventilation. Due to the inherent time delay in executing the control loop, overshoot is inevitable when this happens and the accumulation will quickly result in blood $CO_2$ levels that are substantially above normal. The system described herein substantially minimizes any $CO_2$ build-up and provides sufficient ventilation to expel all exhaled $CO_2$ during hypoventilation immediately through the orifices. The size of the first orifice together with the configuration of the other orifices and deadspace volumes as well as patient's respiratory parameters determines the value at which the relationship between $\dot{v}_{CO_2}$ and $\dot{v}_E$ begins to depart from normal values. The first orifice is sufficiently large to place this first inflection point in the curve 320 at or just below the minimum expected sleeping $\dot{v}_{CO_2}$ (See, FIG. 3).

The first respiratory plateau segment 306 represents an effect of placing a first deadspace volume in the respiratory conduit. Once the first orifice reaches the saturation point, it does not matter how much the patient increases ventilation until such increase overcomes the first deadspace volume by pushing expired $CO_2$ beyond the first deadspace volume and past the second orifice. Hence, increases in ventilation do not result in any additional $CO_2$ excretion until this point is reached. The rate of ventilation at which the first deadspace is overcome and $CO_2$ can flow from the second orifice is defined at the junction of the segment 306 and segment 308.

This respiratory plateau includes a zone where increased respiration above the first inflection point in the curve results in virtually no increase in $\dot{v}_{CO_2}$. This segment has a slope substantially near zero. The existence of this respiratory plateau is due to the fact that the first deadspace volume is larger than the volume of gas that can be expelled through first orifice during the duration of a typical breath. The remaining volume of $CO_2$ is re-inhaled. Any additional $CO_2$ volume within the first deadspace volume does not result in increased levels of excreted $CO_2$. The onset of an unstable respiratory cycle often commences with a progressive narrowing of the airway, resulting in decreasing $\dot{v}_E$. The instability may further develop if decreases in $\dot{v}_E$ are accompanied by proportional decreases in $\dot{v}_{CO_2}$. This gives rise to a build-up of $CO_2$ in the blood sufficiently rapid to cause "overshoot" before the brain can respond to the build-up. The existence of the first respiratory plateau serves to maintain $CO_2$ excretion at a steady level in the face of substantial decreases in $\dot{v}_E$, thus, avoiding a rapid $CO_2$ build-up and preventing substantial "overshoot" as the brain has time to respond to the decrease in ventilation. When recovering from an epoch of low or no ventilation, the first respiratory plateau prevents the increase in $CO_2$ excretion from increasing proportionally to the increase in ventilation. In a similar fashion, this places an obstacle in front of excessive $CO_2$ blow-off that poses the possibility of "undershoot."

The first respiratory plateau segment 306 also permits the clinician to specify a mean arterial level of $CO_2$ for the patient during sleep. Since affected patients are typically at least slightly hypocapnic (i.e., having lower than normal $CO_2$ in arterial blood), it is desirable to reset their sleeping $CO_2$ levels to a value that is closer to normal. The length of the first respiratory plateau segment 306 determines blood $CO_2$ during therapy. Further, since the segment 306 is generated as a result of existence of the first deadspace volume in the mixing device, increasing the size of the first deadspace volume will raise blood $CO_2$ levels. The amount by which any such increase in volume will raise blood $CO_2$ levels can be calculated based on the patient's collected data.

The eucapnic traverse segment 308 represents placement of a second orifice in the respiratory conduit. Until this orifice is saturated (i.e., the point at which the concentration of $CO_2$ in the air flowing from the orifice reaches a maximum), increases in the rate of ventilation ($\dot{v}_E$) result in increases in the rate of $CO_2$ excretion ($\dot{v}_{CO_2}$). The saturation point of the second orifice is defined at the junction of the segment 308 and 310.

Further, segment 308 represents the relationship between $\dot{v}_E$ and $\dot{v}_{CO_2}$ in the range of expected sleeping $\dot{v}_{CO_2}$. Segment 308 is a straight line having a slope that is substantially less than that of the hypoventilatory traverse segment 304. The slope of this relationship as it passes through the actual rate of $CO_2$ production by the patient at a given time establishes the conditions for respiratory stability. The slope is a variable in the relationship describing a closed-loop gain in the respiratory control feedback loop. Since the gain in the control becomes excessive in unstable respiratory syndromes, reducing the slope of the segment 308 in an immediate vicinity of a point where $CO_2$ production and excretion match (i.e., eucapnia) stabilizes respiration.

The slope of the eucapnic traverse segment 308 is governed by multiple variables, such as the first and second deadspace volumes and sizes of the first and second ventilatory orifices. The slope of segment 308 becomes shallower when larger deadspace volumes are used and where the saturation points of the first and second orifices are closer together. The range of $\dot{v}_{CO_2}$ traversed is also determined by the size of the second orifice 133. The measurement of patient's sleeping $\dot{v}_{CO_2}$ permits setting the first respiratory plateau segment 306 at the highest appropriate $\dot{v}_{CO_2}$ level and making the length of the eucapnic traverse segment 308 as short as possible. This achieves a shallow slope of the segment 308.

The second respiratory plateau segment 310 is similar to the first respiratory plateau segment 306, however, segment 310 represents placement of a second deadspace volume in the respiratory conduit. The effects produced are similar to those discussed above with respect to segment 306. The saturation point of the second deadspace volume is defined at the junction of the segment 310 and 312.

The second respiratory plateau segment 310 is disposed above the highest expected sleeping value of $\dot{v}_{CO_2}$ and functions in a manner similar to that of the first respiratory plateau segment 306. It is also a line segment with a nearly zero slope and constitutes a zone where changes in $\dot{v}_E$ result in little or no change in $\dot{v}_{CO_2}$. The length of the second respiratory plateau segment 310 is determined by the volume of the second deadspace. It inhibits $CO_2$ excretion during hyperventilation, as sharp increases in ventilation result in little or no increase in $\dot{v}_{CO_2}$.

The first and second respiratory plateaus segments 306, 310 provide a powerful "ventilatory clamp." While $\dot{v}_{CO_2}$ can vary outside of the zone determined by the two plateaus 306, 310, it will do so in response to a very strong stimulus, e.g., a need to excrete $CO_2$ rapidly after a prolonged obstructive apnea.

The hyperventilatory traverse segment 312 represents placement of an "escape" valve or a third orifice in the respiratory conduit. The third orifice is larger than the other two orifices. This allows escape of $CO_2$ after saturation of the first and second orifices and deadspace volumes. As can be understood by one having ordinary skill in the art, other configurations of orifices and deadspace volumes are possible, thus, resulting in a different graphical representation.

The hyperventilatory traverse segment 312 serves as a safety precaution in the event that it will be necessary to excrete $CO_2$ at a higher than expected rate, e.g., after a lengthy obstructive breathing event. Such excretion generates vigorous breathing at rates that are twice or more the normal rate of ventilation required to achieve such $\dot{v}_{CO_2}$ levels. Without the hyperventilatory traverse there is a risk of developing at least temporary respiratory acidosis under some circumstances. The hyperventilatory traverse is created by the third orifice 135, which can be larger than orifices 131 and 133. The size of the orifice 135 is determined by the ability of the CPAP machine 130 to maintain pressure at maximum flow rates likely to be encountered during treatment. In an embodiment, the orifice 135 is made as large as possible without overtaxing the CPAP machine.

Figure 6:
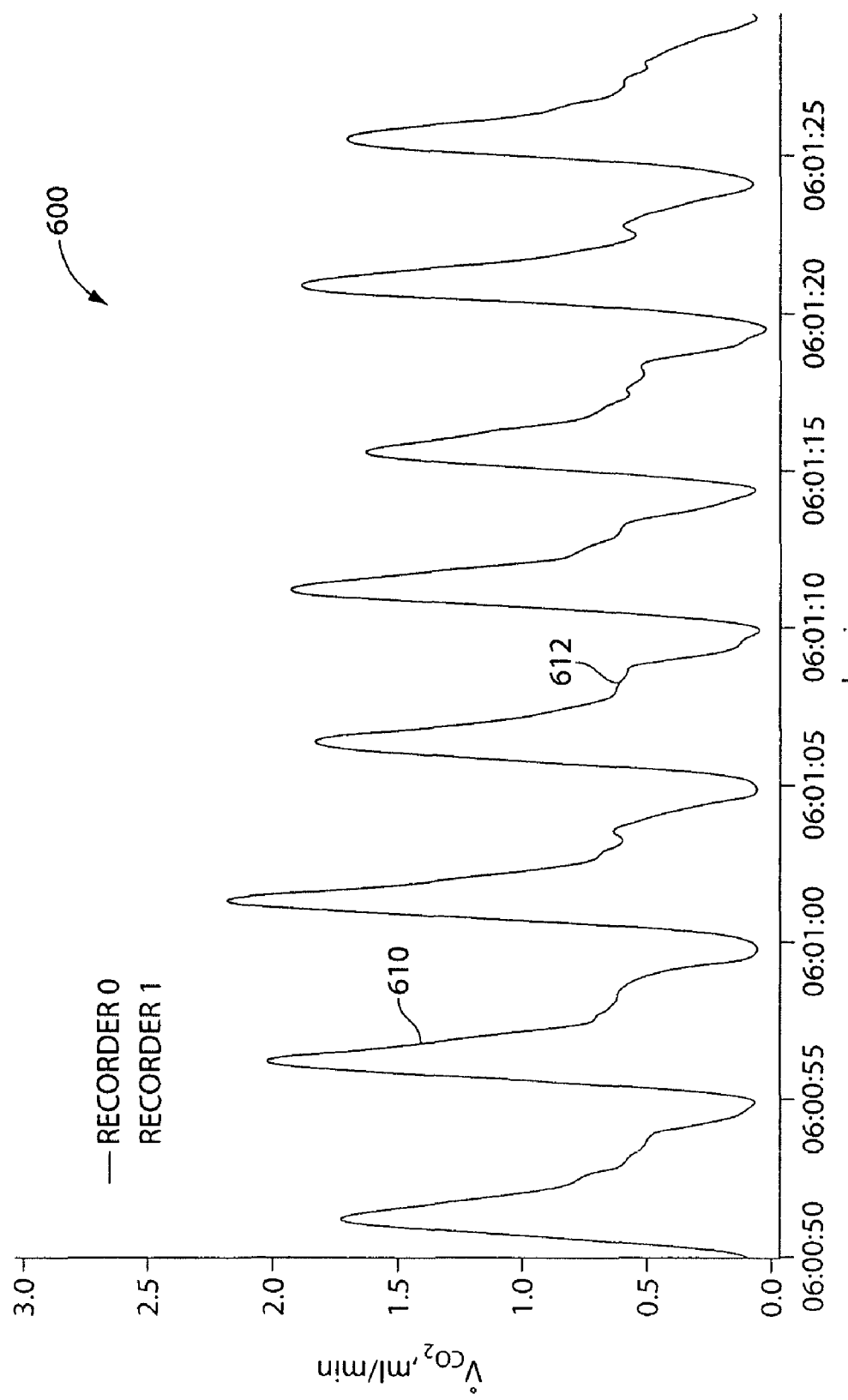
FIG. 6 is a graphical representation of a rate of $CO_2$ escaping from the apparatus for controlling breathing of a patient over the course of eight typical breaths, according to the present invention.

FIG. 6 illustrates a tracing 600 the concentration of $CO_2$ in the air flowing out of all of the orifices of the system together over the course of eight breaths. In this tracing the system is correctly adjusted and a characteristic "hip" 612 develops in the waveform. The existence of this hip is due to the elimination of all exhaled $CO_2$ from the second deadspace at a point in the breathing cycle and thus a cessation of all $CO_2$ flow through the second orifice. Since significant $CO_2$ remains in the first deadspace and in fact the first orifice remains saturated for a further period of time, the flow of $CO_2$ remains briefly at the level of the hip until the first deadspace is fully exhausted. The lack of a hip is an indication that the first orifice is too large and the emergence of a second hip is an indication that the first and second orifices taken together are too small. Thus, the system may be tunable with reference to the morphology of this waveform.

Figure 10:
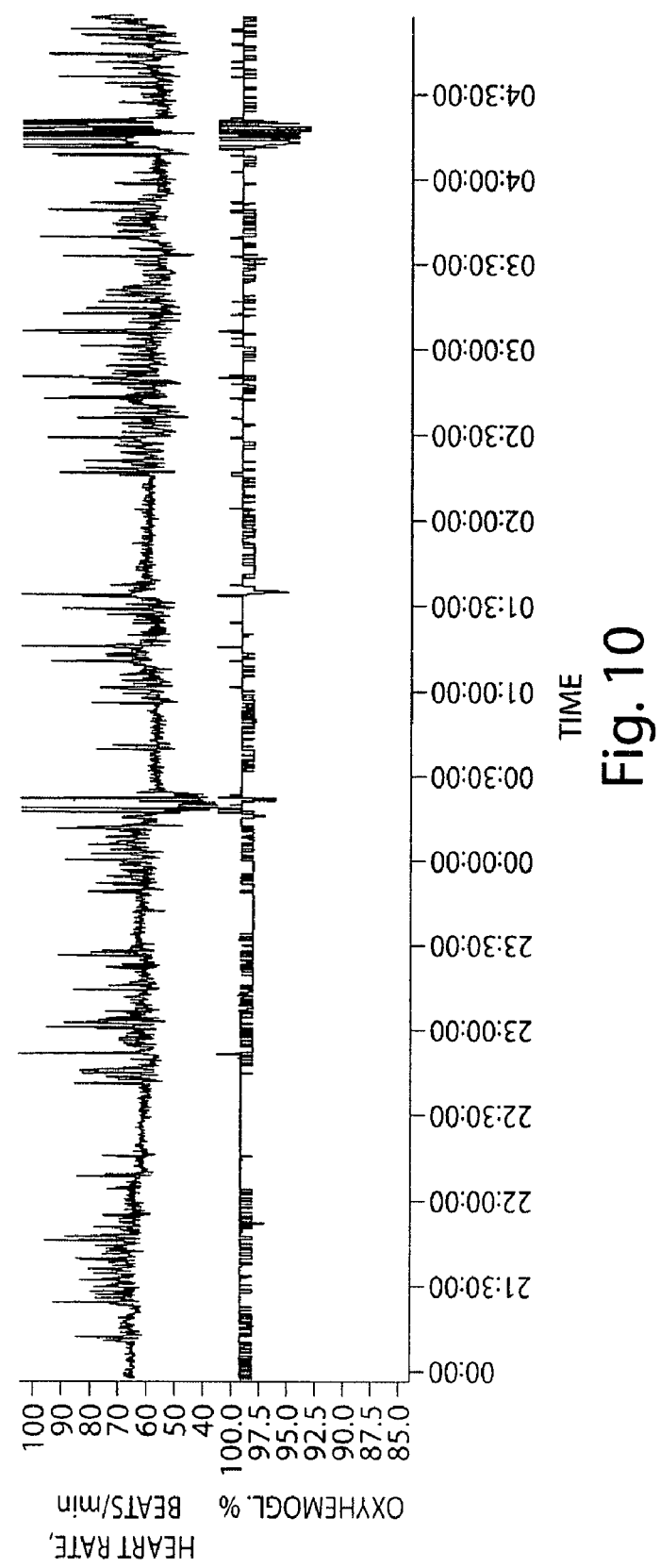
FIG. 10 is a series of tracings showing heart rate and blood oxygen saturation through the night for a patient using conventional methods and systems for controlling breathing.
Figure 11:
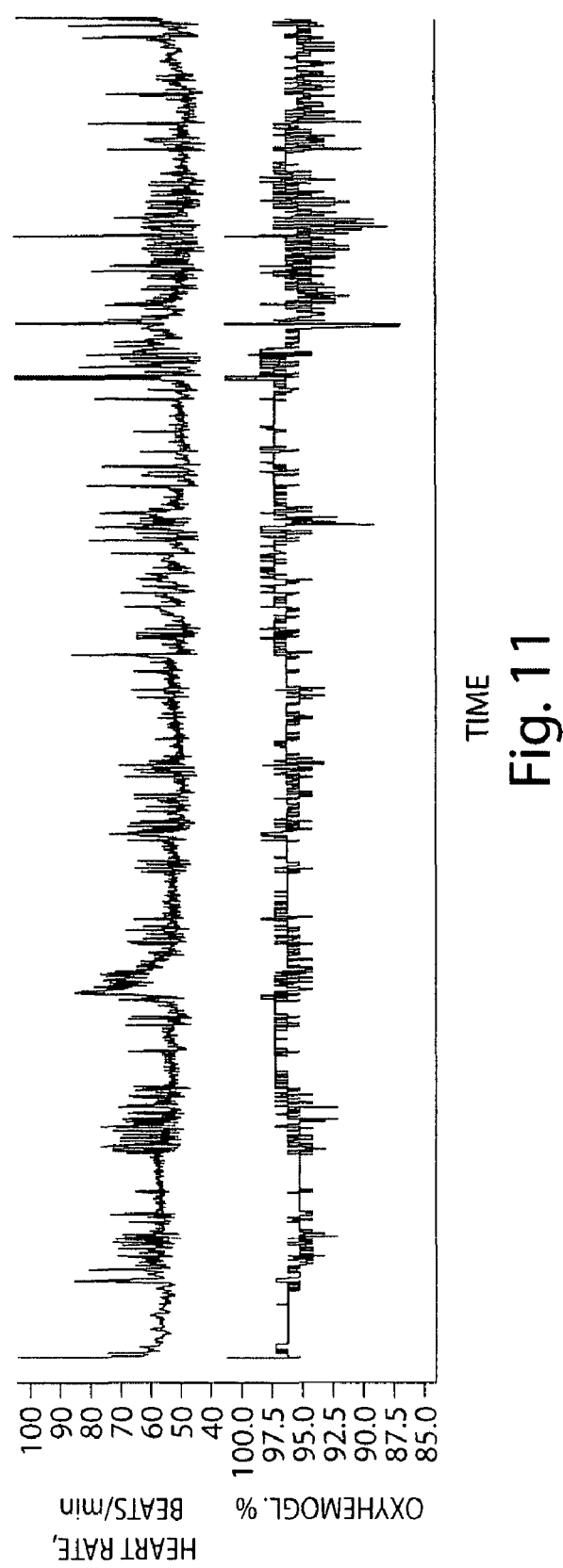
FIG. 11 is a series of tracings showing heart rate and blood oxygen saturation through the night for a patient using a conventional pressurized air supply machine alone.

FIGS. 10-11 illustrate tracings of a heart rate (respective upper portions of the figures) and blood oxygen saturation levels (respective lower portions of the figures) for a patient during a night. The segments of the heart rate tracings containing dense spikes indicate disturbed or fragmented sleep due to frequent arousals originating from a respiratory anomaly. The segments of the heart rate tracings not containing frequent spikes indicate restful or consolidated sleep. FIGS. 10 and 11 illustrate that the affected patient actually gets very few and short periods of consolidated sleep during the night using conventional methods and systems for controlling breathing.

Figure 12:
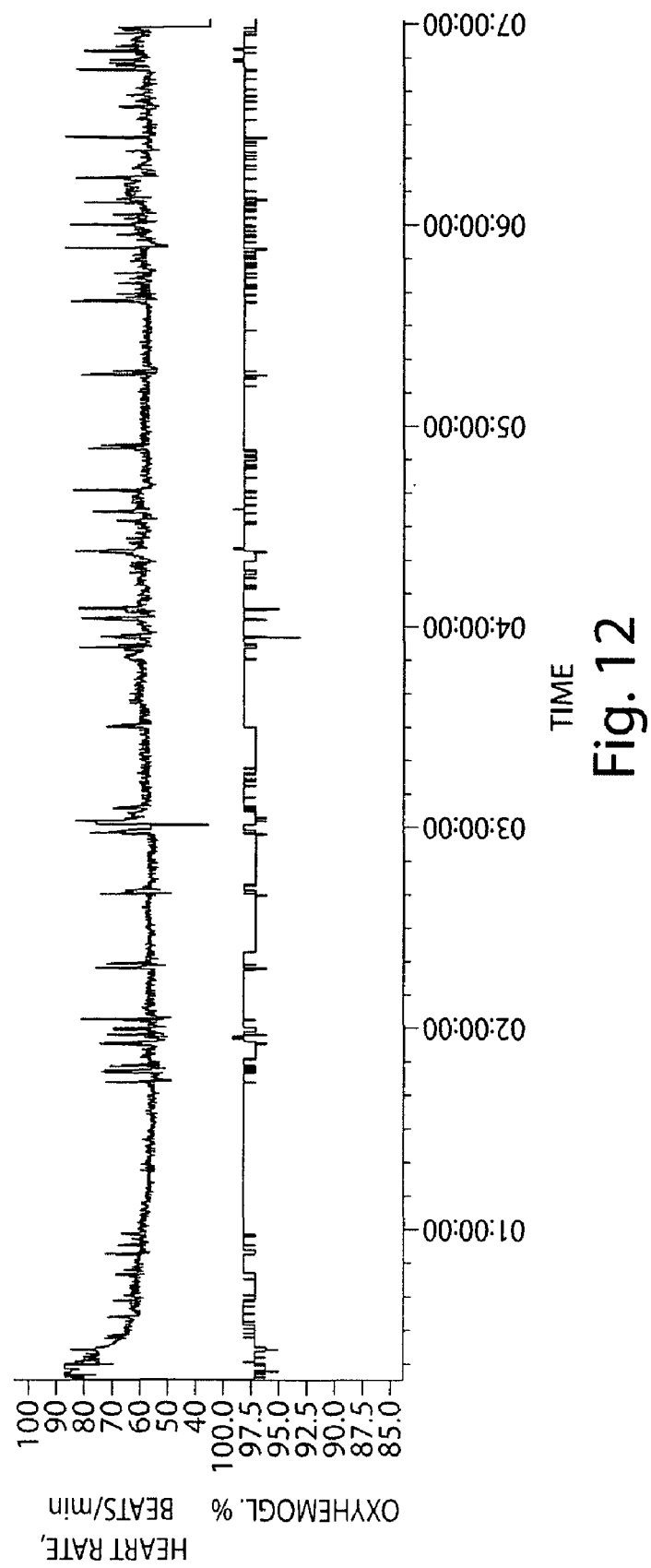
FIG. 12 is a series of tracings showing heart rate and blood oxygen saturation through the night, according the present invention.

FIG. 12 illustrates tracings of heart rate and blood oxygen saturation using the systems and methods discussed in FIGS. 1A-9. The device substantially resolved the frequent arousals, permitting long periods of restful, consolidated sleep. This results in an improvement of symptoms and is indicated by the existence of far fewer spikes in the heart rate tracings, as well as a virtually fixed oxygen tracing. Further, the system described herein has increased the patient's blood oxygen saturation to a level nearly the same as that in FIG. 10, where three liters per minute of supplemental oxygen were being given. The oxygen levels indicated in FIG. 12 were achieved using only the system and no supplemental oxygen. These data indicate that the therapeutic system effectively and reliably eliminates arousals caused by breathing anomalies while maintaining very favorable blood oxygen levels. This provides substantial symptomatic relief to affected patients.

In an exemplary setting, the present invention allows for 2-2.5% improvement in oxyhemoglobin saturation in a patient as compared to free breathing of ambient air. Since the oxyhemoglobin saturation curve is flat at its high end, this represents an important increase in available oxygen at the perfused tissues. Further, the present invention potentially obviates a need for supplemental oxygen in a number of medical settings. Also, by increasing oxygenation the present invention may reduce the sensitivity of the peripheral chemoreceptor, which causes most periodic breathing syndromes.

The present invention forces an increase in the depth of breathing and, thus, the overall rate of ventilation, since the first orifice is configured to saturate at a level that is insufficient to permit excretion of all $CO_2$ being produced by the patient. The patient breathes deeply enough to push $CO_2$ through the first deadspace volume, so that $CO_2$ exits the device through at least the second orifice. By the time patient's inspiratory interval commences, the exhaled gas in various deadspace volumes has been replaced with air and, thus, the concentration of oxygen in the inspired air is only slightly lower than that in the ambient air. Taking the two things together, the increase in breathing more than offsets the slight decline in oxygen content of inspired air ($F_{IO_2}$) to produce greater oxygen transport in the lungs. Conventional single proximal deadspace produces a decrease in $F_{IO_2}$ that more closely matches or exceeds the increase in ventilation and therefore, a frequent need for supplemental oxygen. This is because the deadspace is filled with exhaled breath and remains filled until inhalation commences. Conventional single distal deadspace neither increases ventilation nor decreases $F_{IO_2}$ versus normal breathing, thus, there should be no change in oxygen saturation.

The present invention, as described with respect to FIGS. 1A-12, can be used in the following areas:

1. Recovery from carbon monoxide poisoning. The systems and methods of the present invention speed up the rate of clearance of CO by three to five times relative to the conventionally available methods (e.g., giving oxygen).

2. Prevention of hypocapnia during birth. Hyperventilation by the delivering mother is very common and cuts oxygen supply to the fetus substantially due to a sharp drop in $CO_2$. Low $CO_2$, or hypocapnia, inhibits oxygen transport in many ways. The present invention improves oxygen flow to the fetus during delivery.

3. Recovery from altitude sickness/mountain climbing. The present invention systems and methods without use of the CPAP machine allows quick recovery from this condition.

4. Recovery from ventilator dependency. It is often difficult to wean patients from ventilator dependency, which is a cause of death in a critical care setting. The present invention stimulates breathing and increases oxygenation of the patient allowing the patient to quickly recover.

5. Recovery from anesthesia. This is similar to the recovery from ventilator dependency.

6. Obviating the use of supplemental oxygen in certain chronic lung diseases. Chronic obstructive pulmonary disease is very common and requires expensive oxygen therapy. However, with the present invention there is no need to use such oxygen therapy.

7. As can be understood by one having ordinary skill in the art, other uses of the present invention's systems and methods are possible.

Figure 16A:
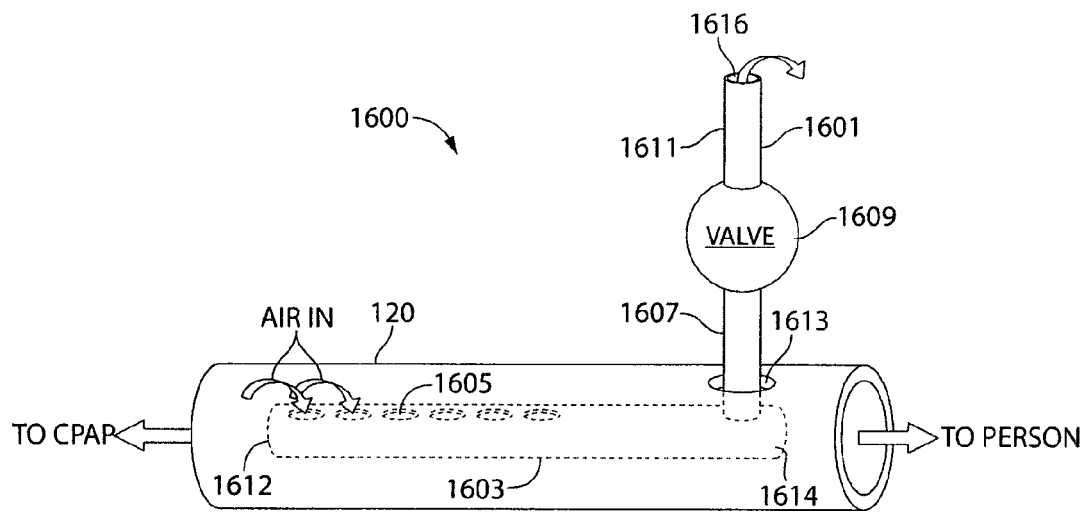
FIG. 16A-B illustrate an alternate system for controlling breathing of a patient, where at least one air flow control device that includes multiple openings, according to the present invention.
Figure 16B:
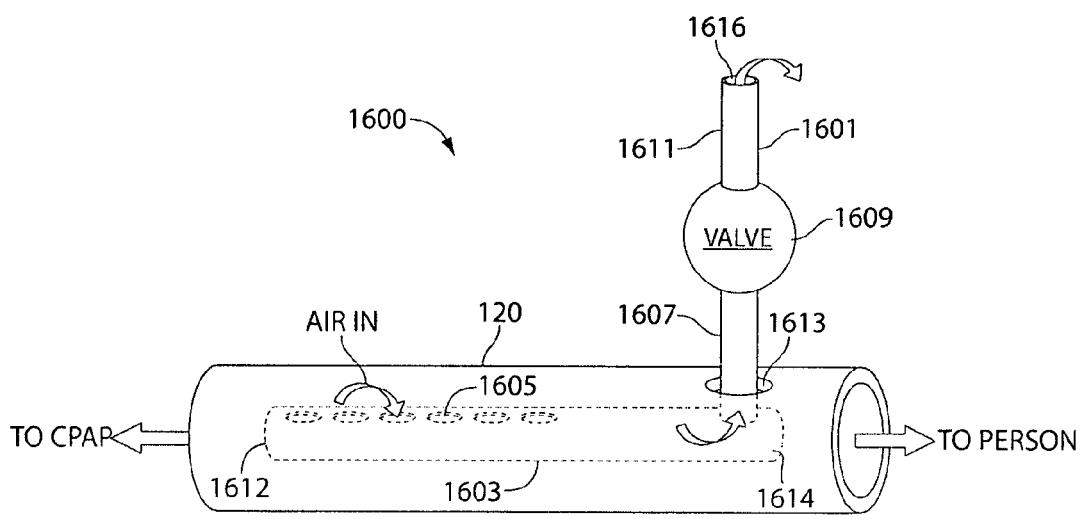

Referring back to FIGS. 1A and 1B, in some alternate embodiments of the present invention, the second orifice 133 is replaced with an airflow control conduit 1601, as shown in FIGS. 16A-B. The airflow control conduit 1601 further includes an orifice tube 1603 that includes multiple openings 1605. The tube 1603 is further coupled to a valve tube 1607 that couples the orifice tube 1603 with a valve 1609. As can be understood by one skilled in the art, the orifice tube 1603 can be configured to be directly coupled to the valve 1609.

As shown in FIG. 16A, the orifice tube 1603 (FIG. 16B illustrates an orifice tube with a closed end) is disposed inside the second volume 113. Further, the valve tube 1607 can also be partially disposed within the second volume 113. The second volume 113 can be configured to include an exit port 1613. The valve tube 1607 protrudes out through the exit port 1613. In some embodiments, the exit port 1613 is configured to create a sealed connection between the valve tube 1607 and the tube containing the second volume 113. Such sealed connection prevents escape of air and/or gas through the exit port 1613. As can be understood by one skilled in the art, the orifice tube 1603 can be configured to be disposed within the first volume 111 and the second volume 113. Alternatively, the orifice tube 1603 can be configured to be disposed only within the first volume 111. As can be further understood by one skilled in the art, the other valves/orifices in the conduit 120 can be replaced with airflow control conduits similar to conduit 1601.

The airflow conduit 1601 can be permanently secured within the second volume 113. Alternatively, the airflow conduit 1601 can be slidably placed within second volume 113 to further control airflow. In some embodiments, the orifice tube 1603 can slide and/or move within the second volume 113. As can be understood by one skilled in the art, such airflow conduits can be placed at any orifice and/or within any volume in the system shown in FIGS. 1A and 1B.

The multiple openings 1605 are configured to be disposed throughout the orifice tube 1603. As shown in FIG. 16, the openings 1605 are placed towards the end 1612 and away from the end 1614 to which the valve tube 1607 is connected. The end 1614 can be configured to be sealed, thus, creating a sealed connection between the orifice tube 1603 and the valve tube 1607. The end 1612 can be an open end, thus, it can be configured to allow air flow through it into the orifice tube 1603.

As can be understood by one skilled in the art, the openings 1605 can be equally spaced out throughout the orifice tube 1603. Alternatively, the openings 1605 can be sporadically placed on the tube 1603. The openings can be configured to be adjustable or controllable. This means that sizes of the openings can be adjusted while the system 100 is in operational state. Alternatively, the sizes of the openings can be fixed. Depending on the desired configuration, the sizes of the openings 1605 can have equal sizes or vary from opening to opening.

The valve 1609 controls evacuation of air from the volume 113. When the valve 1609 is open, the air is being pumped out through the multiple openings 1605 as indicated by the arrows. The air then travels through the orifice tube 1603 into the valve tube 1607 and out through exit port 1616 on the valve tube 1607. When the valve 1609 is closed, no air is being pumped out from the volume 113.

As can be understood by one skilled in the art, the rate of air evacuation from the volume 113 depends on the sizes of the openings 1605. Additionally, the rate can depend on the type of suction device that may be installed in the valve 1609. The valve 1609 can be any conventional valve configured to have an open and a closed position, wherein in the open position, the valve 1609 allows air to be pumped out from the orifice 1603 and/or to travel through the valve tube 1607 to the exit port 1616 and in the closed position, the valve 1609 prevents any air evacuation through the valve tube 1607.

Figure 17:
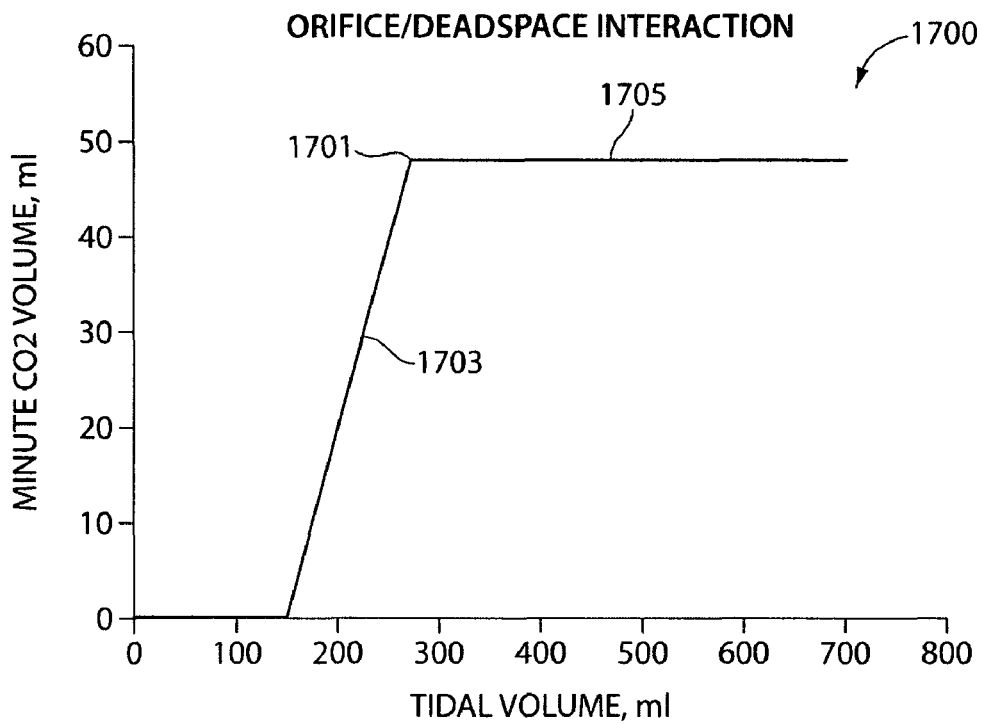
FIG. 17 is a graphical representation of a relationship between depth of breathing (i.e., tidal volume) and $CO_2$ excretion during a single breath by the patient.

As stated above with regard to embodiments shown in FIGS. 1A and 1B, there is a special relationship between an orifice and a volume/deadspace. According to that relationship, the deadspaces contain more volume of air than can be evacuated through an orifice during a single breath. This is illustrated by a curve 1700 having a knee 1701 and a "traverse" segment 1703 and a "plateau" segment 1705. As shown in FIG. 17, the "knee" 1701 appears as breaking point between the traverse and plateau segments.

When a patient breaths normally or healthy, the level of $CO_2$ in his/her lungs is sustained at approximately 5.5% to 6%. When at rest (e.g., sleep), healthy patients breathe less. Such patients can breathe deeper and get as much air in their lungs as needed. Thus, as stated above, a proper level of $CO_2$ is important for healthy breathing, as it serves as one of the regulators of patient's respiratory system, immune system, nervous system and patient's metabolism. As also stated above, a lot of patients suffer from overbreathing, i.e., a form of hidden hyperventilation that "blows off" $CO_2$ from the lungs. Overbreathing reduces the level of $CO_2$ in patient's blood as well. Overbreathing can be treated by reducing a volume of breathing, which normalizes patient's breathing. Normalizing patient's breathing also leads to healthier respiration, strengthened immune system, calmer nervous system and more efficient energy metabolism. On the other hand, having an excess $CO_2$ can also lead to problems. Thus, appropriate levels of $CO_2$ should be maintained in patient's blood.

Figure 18:
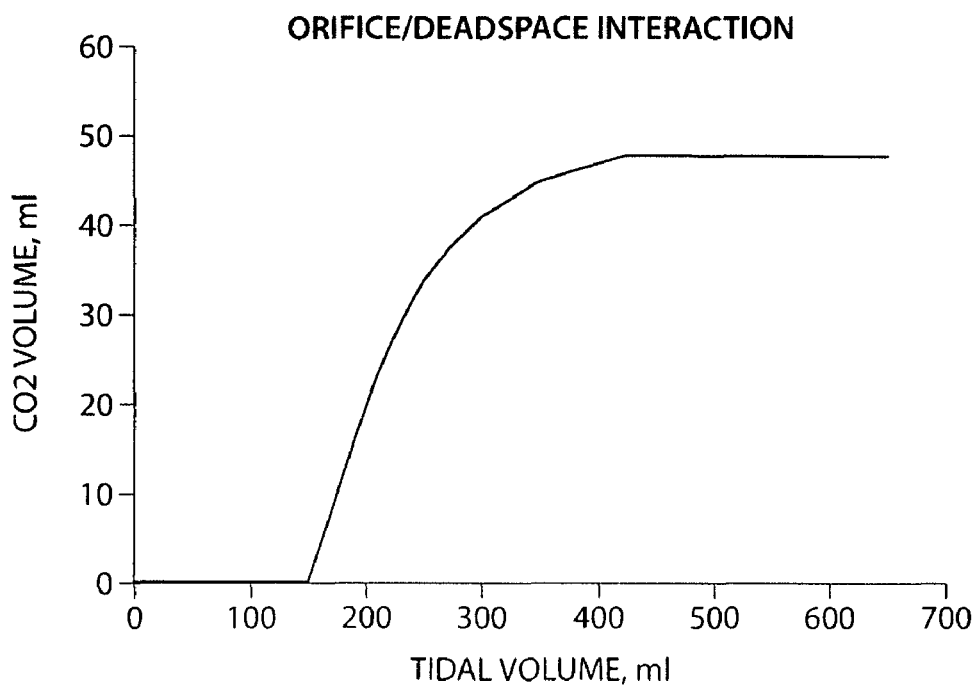
FIG. 18 is a graphical representation of a relationship between depth of breathing and $CO_2$ excretion by the patient, according to an embodiment of the present invention shown in FIG. 16.

As previously mentioned, each breath can be represented by plotting a rate of $CO_2$ excretion as s function of patient's tidal volume. (See, FIG. 17). Since, each breath has a unique shape, the "knee" 1701 may not appear as sharp as shown in FIG. 17. The "knee" may appear "softer" and rounder depending on a particular breath. This is shown in FIG. 18. When second orifice is substituted with the embodiment shown in FIG. 16, the "knee" becomes even "softer".

As also stated above, the slope of the traverse segment 1703 determines patient's respiratory stability, i.e., an ability of a patient to breathe normally during the night. Because of patient's unique physical and physiological characteristics and factors, the slope of the traverse segment 1703 may not be monotonic. In fact, the slope of the traverse segment 1703 decreases throughout the traverse segment, as shown in FIG. 18. The slope of the traverse segment 1703 is based on a complex relationship between orifices and deadspaces/volumes, as stated above with regard to FIGS. 1-15. Thus, placing a tube inside one of the volumes (e.g., through the second orifice as shown in an embodiment of FIG. 16), where the tube includes multiple orifices, allows the system to be tuned along a range of values to further control of the slope of the traverse segment and the system's ability to achieve the slope that best reflects the patient's unique and stable range of breathing value. This means that greater patient's respiratory stability is achieved.

Referring back to FIG. 3, to achieve greater respiratory stability, the slope of the "eucapnic traverse" may be adjusted. Each patient needs a certain decrease in slope that varies from patient to patient. Too much decrease in the slope may present clinical problems for the patient. One example of the clinical problem is that the system shown in FIGS. 1A and 1B may demand too much additional breath volume in order to work properly if the amount of slope decrease is more than necessary. Another example of a clinical problem is that changes in $CO_2$ production by the patient during the night may produce greater changes in blood content of $CO_2$ if the amount of the slope decrease is more than necessary.

Figure 19:
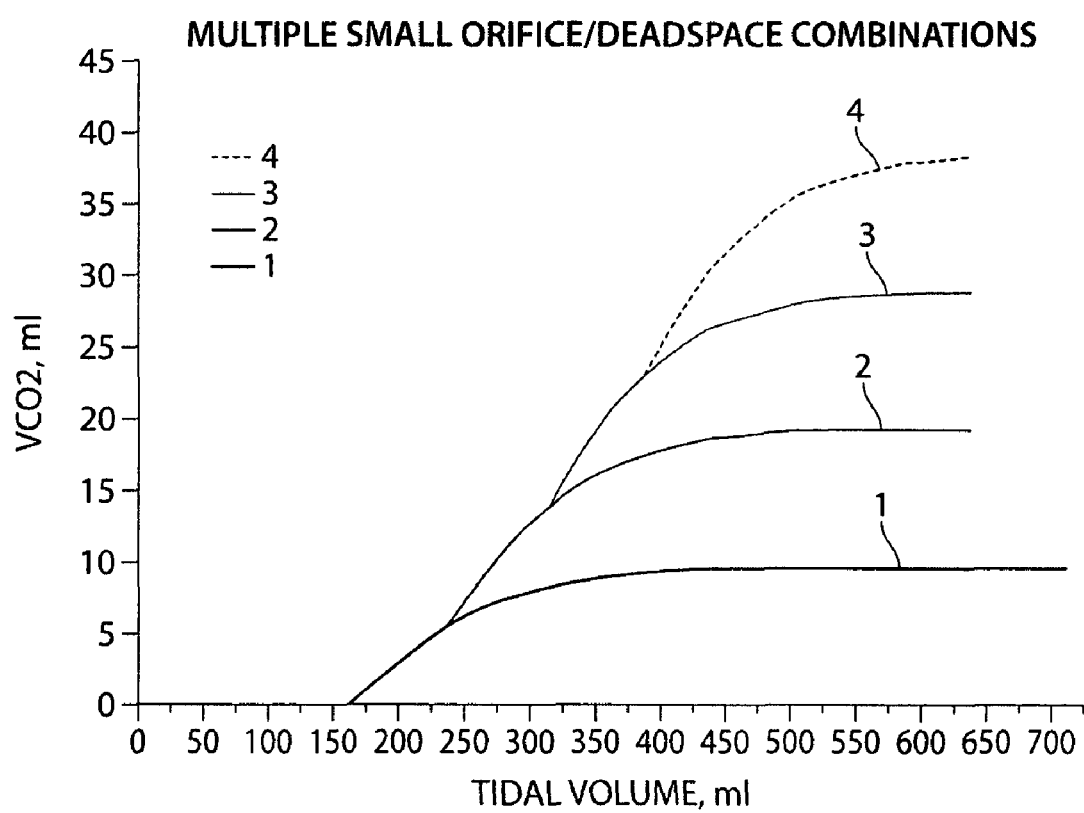
FIG. 19 is another graphical representation of a relationship between depth of breathing and $CO_2$ excretion by the patient, according to an embodiment of the present invention shown in FIG. 16.

The embodiment shown in FIG. 16 solves this problem. FIG. 19 illustrates various slopes of the eucapnic traverse, as obtained when the second orifice is replaced with the airflow control conduit 1601. As stated above, the sizes of orifices in the control conduit 1601 and spaces between the orifices can be specifically selected for each patient. Another alternative solution is to cascade many smaller orifice/deadspace combinations in place of the single second orifice/second deadspace combination. This can be done by perforating the second deadspace in a plurality of places along its length.

The operation of this system is such that the slope of the traverse segment created by the sum of the output of each of the openings 1605 is nearly monotonic and can be adjusted by the valve 1603 governing the evacuation of air out of the tube containing the plurality of orifices. Greater airflow through the tube yields a higher traverse slope and vice versa. Titration of the patient can be achieved by lowering the slope until fundamental stability is attained, and once that is established, no further slope reduction is necessary. Thus, by adjusting the valve 1603, a basic respiratory stability that the system provides for the patient is established. Thus, an advantage of the system is that it provides greater precision, efficacy at minimum required dosage, and fewer side-effects.

Figure 20:
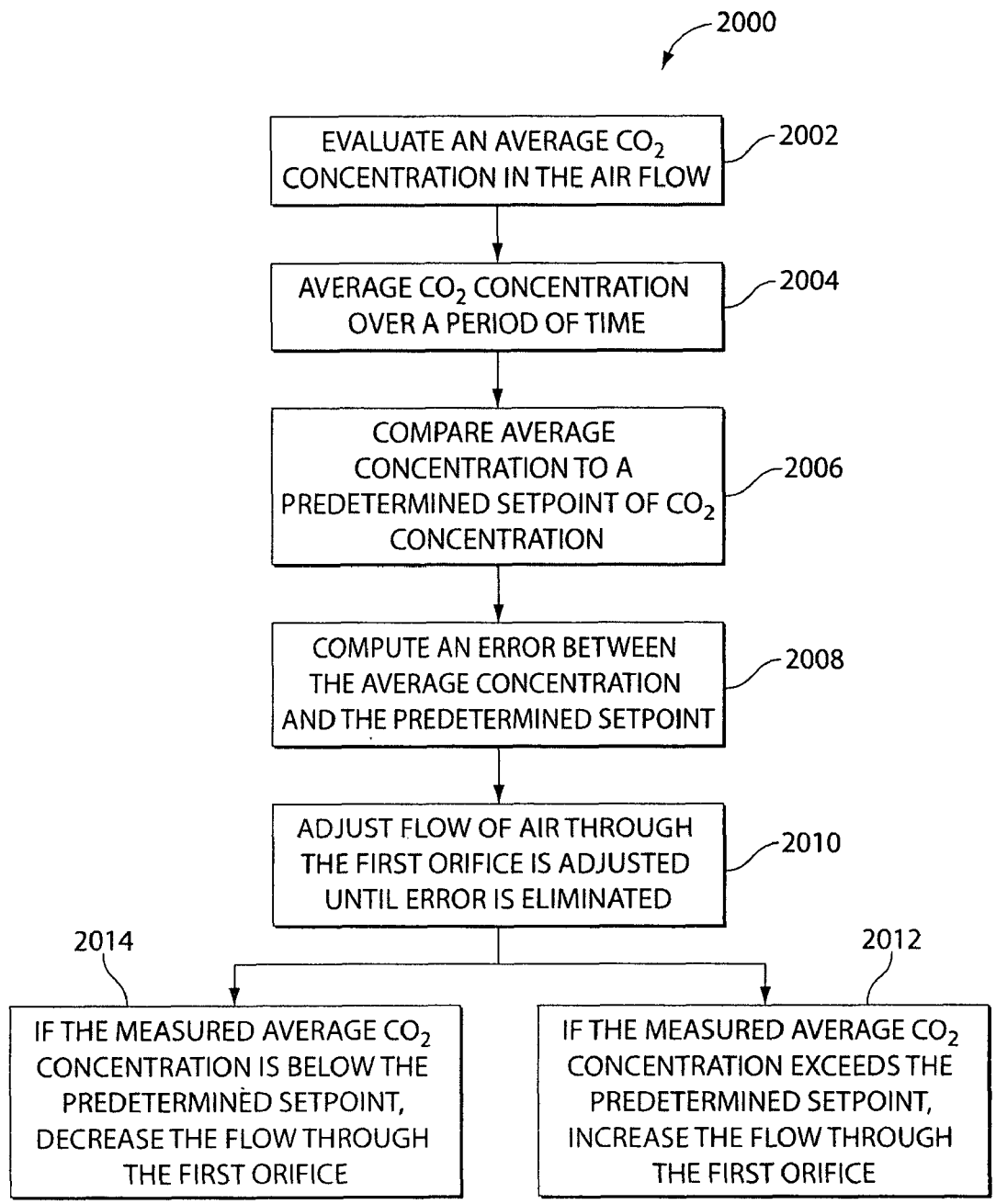
FIG. 20 is an exemplary flow chart of a method for controlling breathing of a patient, according to the present invention.

FIG. 20 illustrates an exemplary method 2000 of adjusting $CO_2$ concentration in the blood of the patient according to an embodiment of the present invention. In some embodiments, a $CO_2$ monitor can be embedded into the second valve (not shown in FIG. 16) to evaluate an average $CO_2$ concentration in the air flowing out of the exit port 1616. (See, step 2002). The $CO_2$ concentration is then averaged over a period of time, as shown in step 2004. The period of time can be set to any time interval (e.g., one minute). The average concentration is compared to a predetermined setpoint of $CO_2$ concentration in the air flowing through exit port 1616. (See, step 2006). This value is dependent on a particular patient and his/her characteristics. In some embodiments, the setpoint may be programmed into the $CO_2$ monitor. Based on the comparison of two values, an error is computed, as indicated in step 2008. In some embodiments, magnitude and direction of the error are determined using a conventional control algorithm such as a proportional integral derivative ("PID") control loop. The PID control loop is a conventional feedback loop used in various control systems. Based on the error, the valve that controls the flow of air through the first orifice is adjusted. The valve adjustment takes place until the computed error is substantially eliminated. For example, if the measured average $CO_2$ concentration exceeds the predetermined setpoint value, the flow through the first orifice is increased. (See, step 2012). If the measured average $CO_2$ concentration is below the predetermined setpoint, the flow through the first orifice is decreased. (See, step 2014). This keeps a "clamp" properly set for the patient's current production of $CO_2$.

As patient's $CO_2$ production varies during the night, the concentration of $CO_2$ in patient's blood also varies. In some embodiments, a solenoid valve (not shown) may be used to switch the embedded $CO_2$ monitor from monitoring and sampling the second orifice to monitoring and sampling the first orifice. Such switching can be done after predetermined periods of time. It can also be done automatically or manually.

The peak value of $CO_2$ concentration in the first orifice is substantially similar or closely correlates to the end-tidal $CO_2$ value and it represents the concentration of $CO_2$ in the patient's blood. Should this value be measured as lower than a normal value, as determined for a patient, the predetermined setpoint value can be increased. If the value is measured as higher than the normal value, the predetermined setpoint value can be lowered. Thus, patient's absolute level of $CO_2$ blood concentration can be maintained well within the normal physiological range. As can be understood by one skilled in the art, the above adjustments can be done manually, automatically, periodically, or at predetermined periods of time. In some embodiments, during a particular sleep stage (e.g., REM sleep) a higher predetermined setpoint value of $CO_2$ as well as higher flow through the second orifice (or the array of orifices shown in FIG. 16) may be used to control the system variables to achieve patient's breathing stability. In some embodiments, the values of the end-tidal $CO_2$ can be determined at various periods of time (e.g., the time periods can be programmed into the present invention's system according to needs of each patient). Based on such end-tidal $CO_2$ determination, the predetermined setpoint value can be adjusted accordingly. In other embodiments, the end-tidal $CO_2$ values can be iteratively determined and based on such iterations, the predetermined setpoint can be adjusted. This allows for accurate tracking of patient's $CO_2$ blood levels and provides greater respiratory stability.

In some embodiments, the concentration of gas flowing through second airflow control device is periodically monitored. Based on that monitoring a value for the end-tidal concentration of $CO_2$ in the gas flowing through the at first airflow device is computed. This represents an estimate of the partial pressure of said $CO_2$ in the arterial blood of the patient. The end-tidal $CO_2$ value is compared to a predetermined range of acceptable end-tidal $CO_2$ values. Then, the predetermined setpoint for concentration of gas flowing through the second airflow control device is adjusted.

Figure 21A:
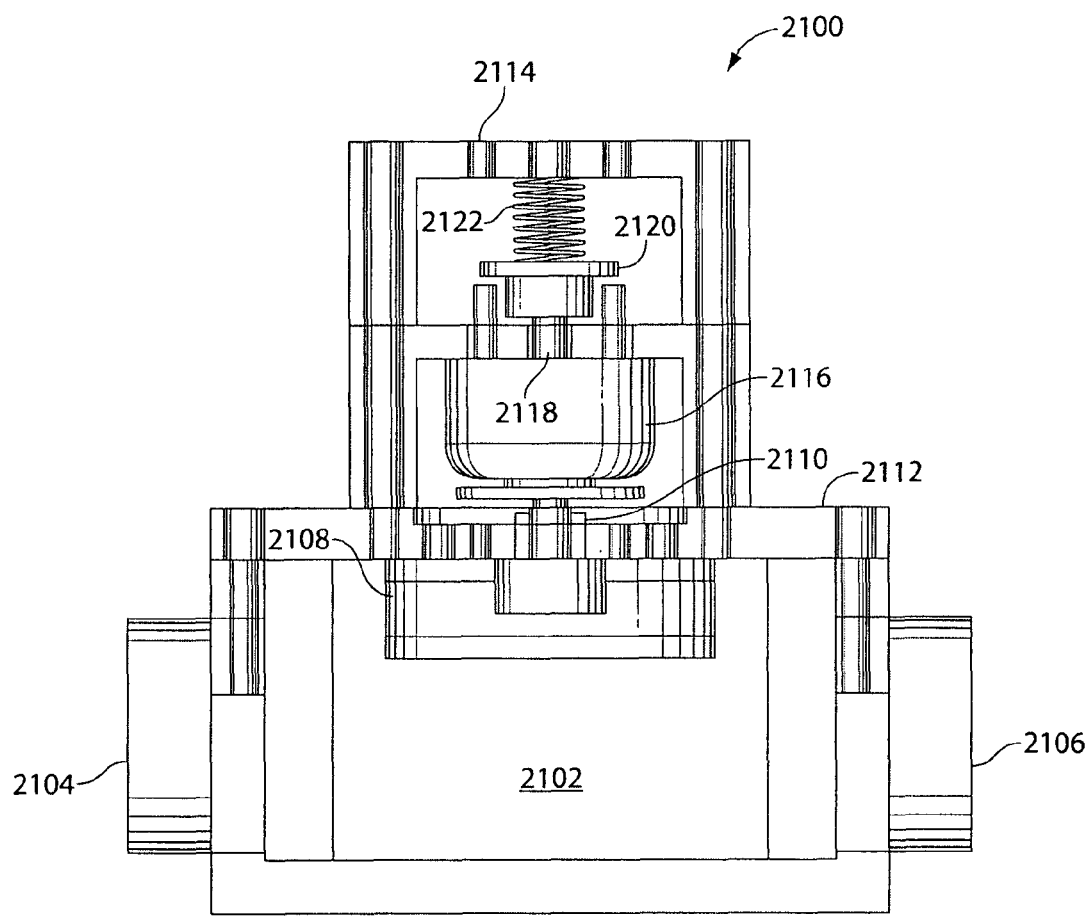
FIGS. 21A and 21B illustrate an exemplary anti-asphyxiation valve, according to the present invention.
Figure 21B:
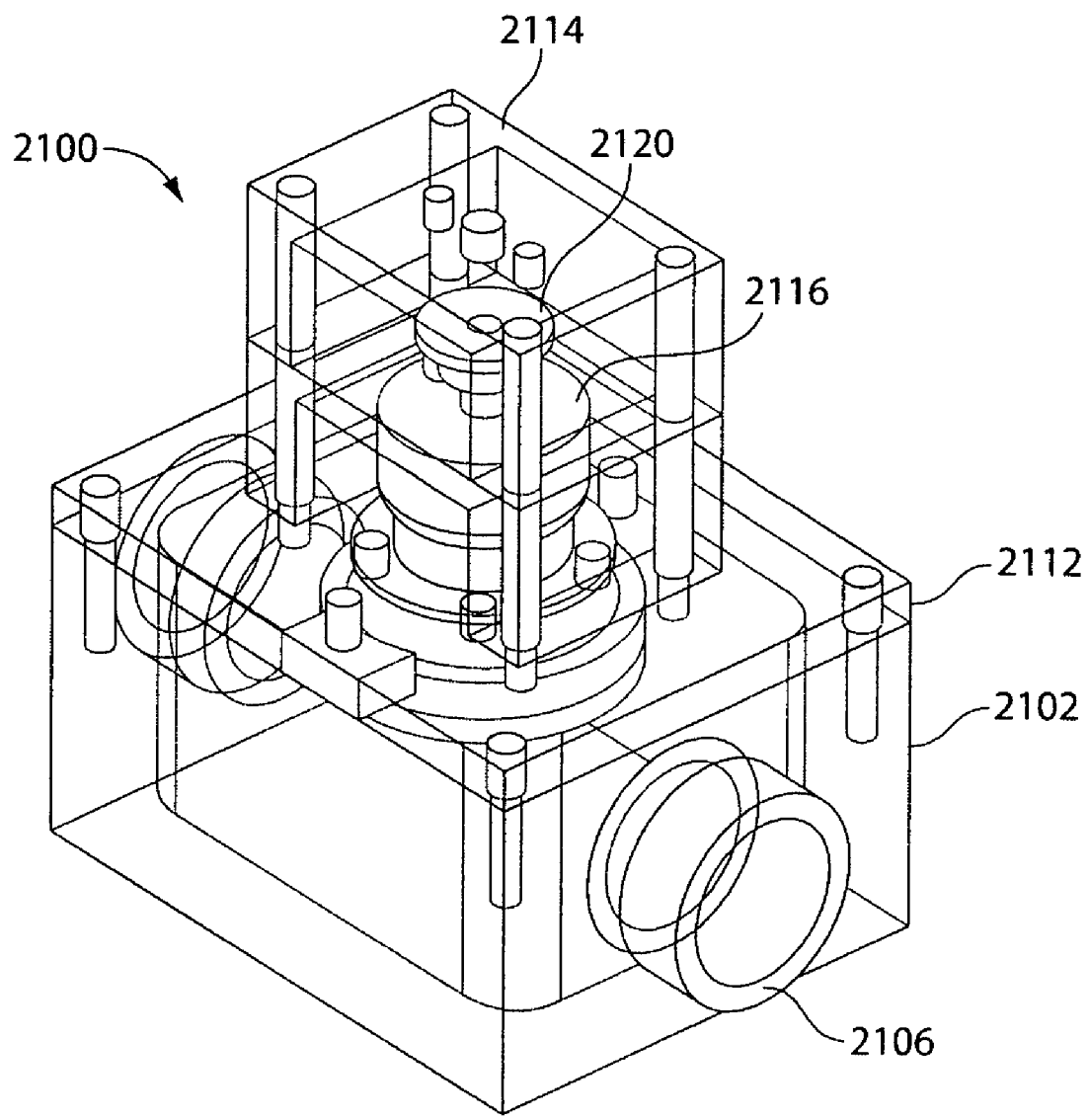

In some embodiments, the system shown in FIGS. 1-20 may be configured to utilize an anti-asphyxiation valve 2100, as shown in FIGS. 21A-B. As stated above, the anti-asphyxiation valve 2100 allows the patient to breathe in the event of failure of the air generating device. In the event of such failure, the valve 2100 opens up and allows the patient to breathe normally. The valve 2100 can be configured to be programmed to allow the patient to breathe freely through the system as the patient falls asleep.

In the event of failure of the air generating device, the valve 2100 is configured to open and allow air flow of approximately 30 lpm (liters per minute) through the patient interface device (i.e., patient's mask). The valve 2100 can be configured to be open in a no-pressure, non-energized state. When the air generating device is properly connected and the air generating device's pressure is on, the valve is configured to be closed.

Referring to FIGS. 21A and 21B, the valve 2100 includes a valve chamber 2102 that is coupled between inlet port 2104 and outlet port 2106 of the airflow conduit shown in FIGS. 1A and 1B. FIG. 21A is a side view of the valve 2100 and FIG. 21B is a three-dimensional view of the valve 2100. The valve chamber is further coupled to a top plate 2112. Valve chamber 2102 further includes a valve cup 2108. The valve cup 2108 is configured to prevent Bernoulli flows from closing valve during heavy breathing. The valve cup 2108 is further coupled to an umbrella valve 2110. The umbrella valve 2110 is configured to be disposed within the top plate 2112. The top plate 2112 is configured to be coupled to an upper portion 2114 of the valve 2100. The upper portion 2114 is configured to enclosed a solenoid body 2116 and a solenoid plunger 2118. The solenoid plunger 2118 further interacts with a spring cup 2120 to open/close the valve 2100. The spring cup 2120 is also coupled to a mechanical return compression spring 2122.

In an embodiment, internal volume of the chamber 2102 is approximately 60 ml. The top plate 2112 is configured to allow ventilation of patient at a rate of approximately 30 lpm. The combination of the solenoid body 2116 and solenoid plunger 2118 are configured to be energized to allow the valve to open and close. The closing and opening of the valve 2100 is achieved using the spring 2120 that transmits force to the solenoid plunger 2118.

The valve 2100 can be configured to have threshold pressure values (e.g., upper and lower) at which the valve either opens or closes. The solenoid body 2116 and solenoid plunger 2118 can be further configured to activate when air generating device pressure starts below a lower threshold value and then surpasses an upper threshold value. Once the solenoid body 2116 and plunger 2118 are activated, the valve 2100 closes. In some embodiments, once the valve 2100 closes and the pressure drops below the upper threshold value, the solenoid components will not be re-activated, thus, the valve will remain closed. The solenoid components will re-activate if the pressure drops below the lower threshold or exceeds the upper threshold. In some embodiments, the lower threshold is defined as 2 cm $H_2O$ and the upper threshold is defined at 6 cm $H_2O$. These thresholds can be adjusted.

Figure 22:
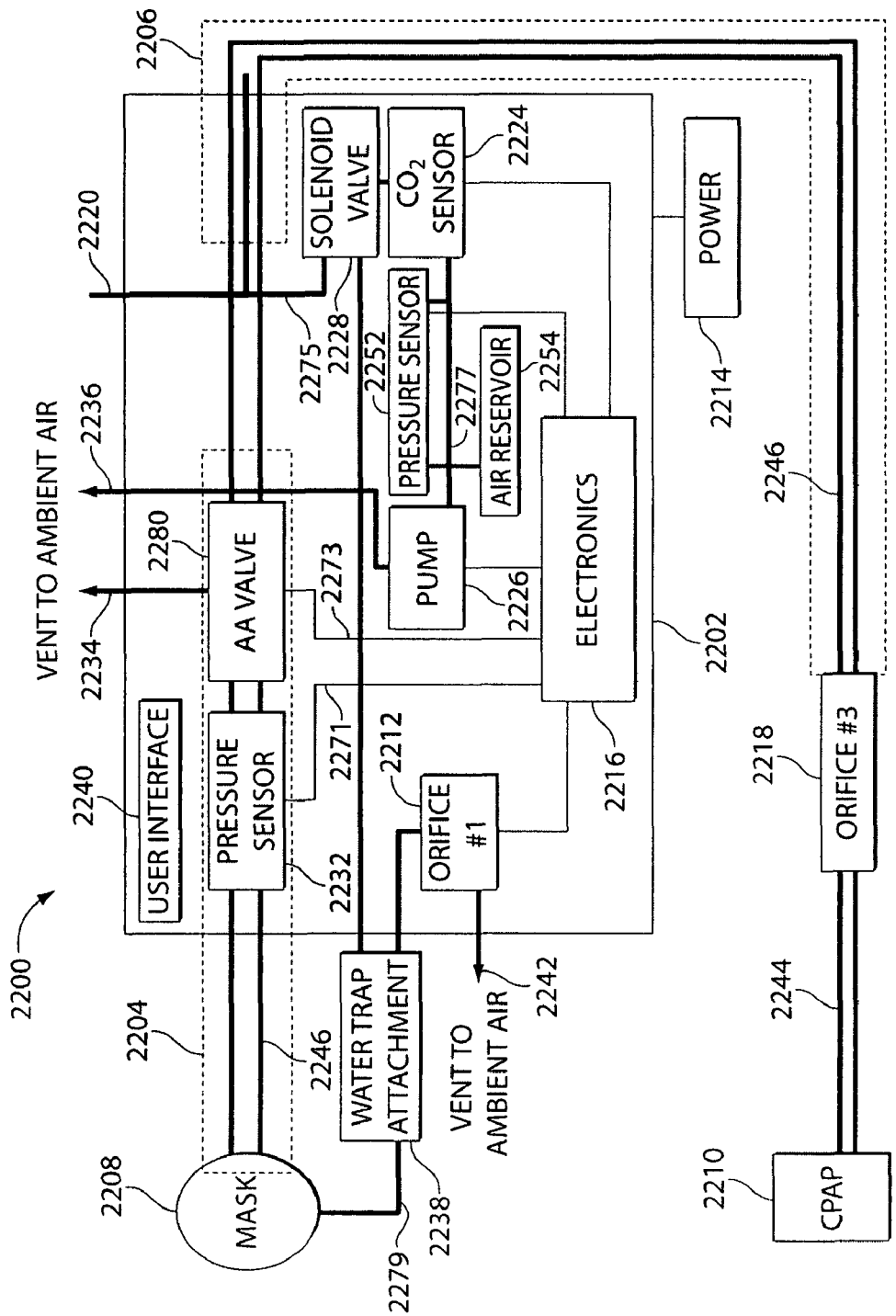
FIG. 22 illustrates another exemplary embodiment of a system for controlling breathing of a patient, according to the present invention.

FIG. 22 illustrates another embodiment of a system 2200 for controlling breathing of a patient, according to the present invention. The system 2200 includes a mask 2208, a first deadspace 2204, a second deadspace 2204, a first orifice 2212, airflow control conduit 2220, a third orifice 2218, a CPAP machine 2210, a connection setup panel 2202. Various components within system 2200 are connected using airway connections (indicated by bold lines in FIG. 22) and/or electronic/electrical connections (indicated by normal lines in FIG. 22).

Similar to the embodiments of FIGS. 1A and 1B, the mask 2208 is configured to be coupled to the first deadspace 2204. The first deadspace 2204 is configured to be disposed between the mask 2208 and the airflow control conduit 2220. The second deadspace 2206 is configured to be coupled to and disposed between the airflow control conduit 2220 and the third orifice 2218. The CPAP machine 2210 is configured to be coupled to the third orifice via connection conduit 2244. As illustrated in FIG. 22, the deadspaces 2204, 2206 are sealed volumes and can be coupled together with the airflow control conduit 2220 extending directly from the deadspaces. In some embodiments, a hose 2246 is configured to run through the deadspaces 2204 and 2206. The hose 2246 can be a 22 mm internal diameter (I.D.) hose. As can be understood by one skilled in the art, the hose can have other I.D. values. The hose 2246 placed inside the second deadspace 2206 is configured to accommodate airflow control conduit 2220 tubes. The airflow control conduit 2220 is discussed above with regard to FIGS. 16A-B.

As shown in FIG. 22, the connection setup panel 2202 further includes a user interface 2240, pressure sensor 2232, AA (anti-asphyxiation) valve 2230, solenoid valve 2228, $CO_2$ sensor 2224, pump 2226, pressure sensor 2252, and electronics box 2216. In some embodiments, the system 2200 may include an air reservoir 2254 that is configured to dampen disturbances in the flow throughout the system. An exemplary volume of the air reservoir 2254 can be set at 10 ml, which, as can be understood by one skilled in the art, can vary according to the parameters of the system 2200. The air reservoir 2254 is configured to be coupled to the pressure sensor 2252. Examples of such air reservoir 2254 can be found in "OEM Compact CO2 Waveform Analyzer, IMPLEMENTATION GUIDE for the OEM CAPNOGRAPHY MODULE", CARDIOPULMONARY TECHNOLOGIES, INC. The components on the connection setup panel 2202 as well as the system 2200 are powered up using a power source 2214. The electronics box 2216 is configured to process information fed to it via a connection 2271 by the pressure sensor 2232 installed in the first deadspace 2204 as well as $CO_2$ sensor 2224. The pressure sensor 2232 is configured to determine air pressure inside the first deadspace 2204. Any changes in air pressure are sent to the electronics box 2216 and based on such changes, the electronics box 2216 can activate an AA valve 2230 using a connection 2273. This means that the electronics box is configured to control opening/closing of AA valve 2230. The AA valve 2230 is discussed above with regard to FIG. 21. The AA valve 2230 is configured to vent to ambient air via airway connection 2234 to allow free breathing of the patient or in the event of a failure of CPAP machine 2210. As can be understood by one skilled in the art, connections 2271 and 2273 are electrical/electronic, or other similar type of connections that can be used to feed information into the electronics box 2216.

The electronics box 2216 also receives information from a 3-way solenoid valve 2228. The valve 2228 is configured to be coupled to the airflow control conduit 2220 via airway connection 2275 to receive $CO_2$ measurements and feed that information to the $CO_2$ sensor 2224, which in turn sends this information the electronics box 2216. Such information allows adjustment of $CO_2$ concentration as discussed above with regard to FIG. 20. The $CO_2$ sensor 2224, the pressure sensor 2252 and the electronics box 2216 also feed information to the diaphragm pump 2226 (via an airway connection 2277), which allows sampling of $CO_2$ concentration using an airway connection 2236.

The electronics box also controls a valve located at the first orifice 2212. The valve at the first orifice 2212 is configured to vent to ambient air 2242 (via an airway connection) based on the measurement of $CO_2$ concentration at the airflow control conduit 2220, as discussed above with regard to FIGS. 16A-20. As stated above, the valve at the first orifice 2212 is configured to be open when the measured $CO_2$ concentration at the airflow control conduit 2220 is high. The valve's flow is reduced and/or the valve is closed when the concentration is low.

In some embodiments, the system 2200 also includes a water-trap attachment 2238 for collection of moisture (and any other unwanted elements) from the mask 2208 (via airway connection 2279) and/or conduits 2246, deadspace volumes 2204, 2206 or any other components in the system. As shown in FIG. 22, the water-trap attachment 2238 is configured to be coupled between the mask 2208 and the first orifice 2212.

In some embodiments of the present invention, the first orifice 2212 is configured to allow a rate of airflow of 0-10 lpm. The airflow conduit 2220 is configured to allow a rate of airflow of 5 lpm at a pressure of 10 cm $H_2O$. The rate of airflow from the airflow conduit is patient dependent, as discussed above with regard to FIGS. 16A-20. The third orifice is configured to allow a rate of airflow of 20 lpm. The first deadspace 2204 is configured to have a volume of 300 ml. The second deadspace is configured to have a volume of 400 ml. As can be understood by one skilled in the art, the volumes and rates of flow are patient-specific and the above quantities are given for non-limiting exemplary purposes. As can be further understood by one skilled in the art, other configurations of system 2200 are possible.

Example embodiments of the methods, circuits, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A system for controlling breathing of a patient, comprising:
    a respiratory conduit;
    said respiratory conduit is configured to be coupled to a patient interface device;
    said respiratory conduit is further configured to be coupled to a pressurized air generating device;
    said respiratory conduit includes a first, second, and third air flow control devices, positioned between said patient interface device and said pressurized air generating device, each of said air flow control devices defines an orifice being in communication with ambient air; and
    said respiratory conduit includes at least two volumes, wherein one volume is positioned between said first air flow control device and said second air flow control device and a second volume is positioned between said second air flow control device and said third air flow control device;
    wherein said volumes are partial dead space volumes configured to accumulate at least a portion of breath expired by the patient;
    wherein said first, second, and third air flow control devices are configured to control a rate of excretion of carbon dioxide from said respiratory conduit and a concentration of said carbon dioxide in blood of the patient; and
    wherein said second airflow control device comprises an internal conduit being disposed within said second volume in a substantially coaxial configuration, said internal conduit defining multiple openings along a longitudinal axis, said internal conduit being coupled to a valve that is configured to control evacuation of carbon dioxide from within said second volume to the ambient air.

2. A method for controlling flow of carbon dioxide to a patient, comprising controlling a level of carbon dioxide in blood of the patient using the system of claim 1;
    wherein said controlling includes:
        measuring airflow through at least one of said airflow control devices;
        detecting a content of carbon dioxide in the measured airflow;
        adjusting airflow through at least one other one of said airflow control devices based on said detecting of said concentration of carbon dioxide; and
        adjusting sizes of said volumes based on said detection of said concentration of carbon dioxide and said adjusting of said airflow through at least one of said air flow control devices,
    wherein the patient interface device creates a substantially sealed connection between the conduit and an airway of the patient.

3. The method according to claim 2, wherein said adjusting sizes step further comprises
    adjusting sizes of said volumes and said airflow through at least one of said airflow control devices based on a relationship between $\dot{v}_{CO_2}$ and $\dot{v}_E$, wherein $\dot{v}_{CO_2}$ is a rate of excretion of carbon dioxide by the patient per minute; $\dot{v}_E$ is a total rate of ventilation per minute by the patient.

4. The method according to claim 3, wherein a curve representing said relationship between $\dot{v}_{CO_2}$ and $\dot{v}_E$ contains at least two discontinuities;
    said discontinuities are determined using the lengths of
        a hypoventilatory traverse segment caused by a placement of said first airflow control device in the system;
        a first respiratory plateau segment caused by a placement of said first volume in the system;
        at least one eucapnic traverse segment caused by a placement of said multiple openings in said second airflow control device;
        a second respiratory plateau segment caused by a placement of said second volume in the system; and
        a hyperventilatory traverse segment caused by a placement of said third airflow control device in the system.

5. The method according to claim 4, wherein said hypoventilatory traverse segment has a slope defined by a relationship between volume of air breathed by the patient during a breathing interval and an amount of carbon dioxide exhaled by the patient in said breathing interval.

6. The method according to claim 4, wherein during said eucapnic traverse segment, an additional volume of carbon dioxide escapes from at least one of said multiple openings of said second airflow control device, wherein said additional volume is determined based on the volume of carbon dioxide that escaped from said first airflow control device.

7. The method according to claim 4, wherein during said hyperventilatory traverse segment, an additional volume of carbon dioxide escapes from said third airflow control device, wherein said additional volume is determined based on a volume of carbon dioxide that escaped from at least said first and second airflow control devices.

8. The method according to claim 3, wherein said controlling further includes determining a target mean arterial concentration of carbon dioxide based on said adjusting sizes step.

9. The method according to claim 3, wherein said adjusting sizes step is automatic.

10. The method according to claim 3, wherein said adjusting sizes step is manual.

11. The system according to claim 1, wherein said patient interface device is selected from a group consisting of a nasal mask, an oral mask, an orofacial mask, a nasal prong device, an intra-oral device, and an endotracheal tube.

12. The system according to claim 11, wherein said patient interface device is configured to create a substantially sealed connection between said respiratory conduit and a breathing airway passage of the patient.

13. The system according to claim 1, wherein said respiratory conduit includes an auxiliary air flow control device located substantially adjacent to said patient interface device configured to control flow of air to the airway of the patient.

14. The system according to claim 13, wherein said auxiliary air flow control device is controlled by the patient.

15. The system according to claim 1, wherein said respiratory conduit includes an anti-asphyxiation valve configured to create an access to air and to bypass said respiratory conduit, if said pressurized air generating device fails, and located substantially adjacent to said patient interface device.

16. The system according to claim 1, wherein said air flow control devices are configured to adjust a rate of carbon dioxide flow through said air flow control devices based on at least one physiological variable of the patient.

17. The system according to claim 1, wherein said air flow control devices and said volumes are configured to control
   a rate of excretion of carbon dioxide from said respiratory conduit; and
   a concentration of said carbon dioxide in the blood of the patient.

18. The system according to claim 17, wherein said air flow control devices and said volumes are configured to allow a range of amounts of said carbon dioxide readily excreted from said respiratory conduit to be equal to a range of production of said carbon dioxide by the patient.

19. The system according to claim 1, wherein said first air flow control device is configured to allow an escape of an amount of carbon dioxide that is lower than or equal to the amount of said carbon dioxide produced by the patient at a time.

20. The system according to claim 19, wherein said second air flow control device is configured to allow an escape of an amount of said carbon dioxide that is based on
   said amount of carbon dioxide allowed to escape from said first air flow control device, and
   a maximum total amount of carbon dioxide produced by the patient at a time.

21. The system according to claim 19, wherein said third air flow control device is configured to allow an escape of air that is based on said amount of air allowed to escape from said first and said second air flow control devices to prevent re-breathing of excess amount of said carbon dioxide by the patient.

22. The system according to claim 1, wherein
   said respiratory conduit is configured to be rotatably coupled to said patient interface device.

23. The system according to claim 1, wherein said respiratory conduit includes a protective cover configured to prevent damage to said respiratory conduit.

24. The system according to claim 1, further comprising a collector configured to be coupled to said respiratory conduit and further configured to collect condensation during breathing of the patient.

25. A method of controlling breathing of a patient, wherein air is supplied to the patient using a patient interface device coupled to an air supply device using a respiratory conduit that includes a first, second, and third air flow control devices, positioned between the patient interface device and a pressurized air generating device, and first and second volumes, wherein the second volume is configured to allow withdrawal of air from at least one location within the second volume to ambient air using the second air flow control device, the method comprising:
   determining an average concentration of carbon dioxide in the air flowing out of the second air flow control device to the ambient air, the second airflow control device being further from the patient interface device than the first airflow control device;
   comparing the average concentration of carbon dioxide to a predetermined setpoint value of concentrate on of carbon dioxide;
   computing the difference between the average concentration and the predetermined setpoint value of concentration;
   controlling the breathing of the patient by adjusting flow of air through the first air flow control device to the ambient air until the computed difference is substantially eliminated.

26. The method according to claim 25, further comprising
determining concentration of carbon dioxide flowing through at least one airflow control device; and
   adjusting the flow of air through at least another airflow control device based on the concentration of carbon dioxide flowing through the at least one airflow control device.

27. The method according to claim 26, further comprising
determining whether the concentration of carbon dioxide flowing through the at least one airflow control device exceeds the predetermined setpoint value; and
   increasing a flow of air through at least another airflow control device.

28. The method according to claim 26, further comprising
determining whether the concentration of carbon dioxide flowing through the at least one airflow control device is below the predetermined setpoint value; and
   decreasing a flow of air through the at least another airflow control device.

29. The method according to claim 25, wherein the predetermined setpoint value is calculated for the patient.

30. The method according to claim 25, further comprising
periodically monitoring concentration of carbon dioxide flowing through at least one airflow control device;
   computing a value for the end-tidal concentration of carbon dioxide in said air flowing through the at least one airflow device, which represents an estimate of the partial pressure of said $CO_2$ in the arterial blood of the patient;
   comparing said end-tidal $CO_2$ value to a predetermined range of acceptable end-tidal $CO_2$ values; and
   adjusting the predetermined setpoint for concentration of carbon dioxide flowing through the at least one airflow control device based on said comparing.

31. The method according to claim 30, further comprising
determining whether the computed end-tidal $CO_2$ value is lower than the range of acceptable end-tidal $CO_2$ values; and
   increasing the predetermined setpoint value of concentration of carbon dioxide flowing through the at least one airflow control device.

32. The method according to claim 30, further comprising
determining whether the computed end-tidal $CO_2$ value is higher than the range of acceptable end-tidal $CO_2$ values; and
   decreasing the predetermined setpoint value of concentration of carbon dioxide flowing through the at least one airflow control device.

33. The method according to claim 25, further comprising
determining whether the patient is in a particular sleep stage;
   adjusting at least one parameter based on the particular sleep stage.

* * * * *